United States Patent [19]

Tachibana et al.

[11] Patent Number: 4,916,051

[45] **Date of Patent: * Apr. 10, 1990**

[54] SILVER HALIDE COLOR PHOTOGRAPHIC LIGHT-SENSITIVE MATERIAL

[75] Inventors: Kimie Tachibana, Tokyo; Yutaka Kaneko, Sagamihara, both of Japan

[73] Assignee: Konica Corporation, Tokyo, Japan

[*] Notice: The portion of the term of this patent subsequent to Oct. 10, 2006 has been disclaimed.

[21] Appl. No.: 177,987

[22] Filed: Apr. 5, 1988

[30] Foreign Application Priority Data

| | | | |
|---|---|---|---|
| Apr. 7, 1987 | [JP] | Japan | 62-85510 |
| Apr. 7, 1987 | [JP] | Japan | 62-85511 |
| May 13, 1987 | [JP] | Japan | 62-114838 |

[51] Int. Cl.$^4$ .......... G03C 7/38

[52] U.S. Cl. .......... 430/558; 430/384; 430/385

[58] Field of Search .......... 430/384, 385, 558

[56] References Cited

U.S. PATENT DOCUMENTS

| | | | |
|---|---|---|---|
| 2,367,531 | 6/1945 | Salminen et al. | 430/376 |
| 2,369,929 | 7/1945 | Vittum et al. | 430/376 |
| 2,423,730 | 4/1947 | Salminen et al. | 564/174 |
| 2,772,162 | 12/1956 | Salminen et al. | 430/384 |
| 3,880,661 | 2/1975 | Lau et al. | 430/385 |
| 4,122,369 | 7/1978 | Hughes et al. | 313/430 |
| 4,764,456 | 8/1988 | Watanabe et al. | 430/558 |

FOREIGN PATENT DOCUMENTS

| | | | |
|---|---|---|---|
| 57-155538 | 9/1982 | Japan . | |
| 57-157246 | 9/1982 | Japan . | |
| 2196662 | 8/1987 | Japan | 430/558 |
| 2275260 | 11/1987 | Japan | 430/558 |
| 2125349 | 6/1989 | Japan | 430/558 |

OTHER PUBLICATIONS

Mees and James, *The Theory of The Photographic Process*, 3rd Edition p. 387.

Morrison and Boyd, *Organic Chemistry*, 3rd Edition, pp. 27–29.

*Primary Examiner*—Paul R. Michl
*Assistant Examiner*—Lee C. Wright
*Attorney, Agent, or Firm*—Finnegan, Henderson, Farabow, Garrett and Dunner

[57] ABSTRACT

A silver halide color photographic light-sensitive material containing an improved cyan dye-forming coupler is disclosed. The cyan dye-forming coupler is selected from pyrazoloazole compounds, pyrazolotriazole compounds and benzpyrazolotriazole compound represented by Formulas [I] through [VI] as disclosed in the description.

20 Claims, 2 Drawing Sheets

SILVER HALIDE COLOR PHOTOGRAPHIC LIGHT-SENSITIVE MATERIAL

FIELD OF THE INVENTION

This invention relates to a silver halide color photographic light-sensitive material containing a novel cyan dye-forming coupler and more particularly to a silver halide color photographic light-sensitive material containing a cyan dye-forming coupler excellent in spectral absorption characteristics.

BACKGROUND OF THE INVENTION

A color image is formed by exposing a silver halide photographic light-sensitive material to light and then treating the light-sensitive material in a color development process in which an oxidized aromatic primary amine color developing agent is reacted with a dye-forming coupler (this term will sometimes be referred to simply as 'coupler') so as to form a dye.

Generally, to the above-mentioned photographic process, a color reproduction method using a color subtraction technique is applied, so that color images in yellow, magenta and cyan may be formed, respectively.

As for the cyan color image dye-forming couplers, phenols or naphthols have popularly been used so far.

From the viewpoint of color reproduction, however, cyan images obtained from phenols or naphthols have had serious problems. Namely, there have been the poor sharpness of spectral absorption on the short wavelength side as well as an undesirable absorption, i.e., an irregular absorption, in green spectral region. The present situation is that, with a negative light-sensitive material, therefore, it cannot help masking or taking some measure to remedy the irregular absorption: and with a paper light-sensitive material, there have not been any remedying measures, but the color reproducibility thereof has considerably been worsened.

With dye images obtained from phenols and naphthols having so far been used, there have still been several unsolved problems in their preservability. For example, the dye images obtained from 2-acylaminophenol cyan coupler described in U.S. Pat. Nos. 2,367,531 and 2,423,730 are generally poor in fastness against heat; the dye images obtained from 2,5-diacylaminophenol cyan coupler described in U.S. Pat. Nos. 2,369,929 and 2,772,162 are generally poor in fastness against light; and dye images obtained from 1-hydroxy-2-naphthamide cyan coupler are generally poor in fastness against both light and heat. They have therefore been unsatisfactory.

Also, with 2,5-diacylaminophenol cyan couplers described in U.S. Pat. No. 4,122,369, Japanese Patent Publication Open to Public Inspection (hereinafter called Japanese patent O.P.I. Publication) Nos. 155538-1982 and 157246-1982, and so forth, and 2,5-diacylamino phenol cyan coupler having a hydroxy group in the ballast portion thereof described in U.S. Pat. No. 3,880,661, each of them has still been unable to reach a satisfactory level, from the viewpoints of the fastness against light and heat and yellow-stain prevention.

Whereas, the present inventors have studies variously on the above-mentioned problems. Resultingly, they have discovered that a substance having a hydrogen-bondable group in the pyrazolotriazole nucleus thereof may be able to give desired results, so that they have accomplished this invention.

SUMMARY OF THE INVENTION

It is, therefore, an object of the invention to provide a silver halide color photographic light-sensitive material containing a novel cyan coupler having a hydrogen-bondable group.

Another object of the invention is to provide a silver halide color photographic light-sensitive material containing a novel cyan coupler corrected the above-mentioned defects of the cyan couplers having been used so far, wherein, namely, the spectral absorption thereof may be sharpened and the absorption in the green spectral region is reduced, so that a clear cyan image excellent in spectral absorption characteristics can be formed.

A further object of the invention is to provide a silver halide color photographic light-sensitive material containing a novel cyan coupler capable of forming a cyan image without causing any change in hue against heat and moisture.

The above-mentioned objects and other advantages of the invention can be accomplished with a silver halide color photographic light-sensitive material comprising a support bearing at least one silver halide emulsion layer thereon, wherein the above-mentioned silver halide emulsion layer contains at least one cyan dye-forming coupler selected from the group consisting of those represented by the following Formulas [I], [II], [III], [IV], [V] and [VI].

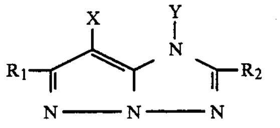

Formula [I]

wherein X represents a hydrogen atom or a substituent capable of being split off upon reaction with the oxidized product of a color developing agent, Y represents a hydrogen atom or a substituent, and $R_1$ and $R_2$ independently represent a hydrogen atom, a substituent or a group having an active hydrogen atom capable of forming a hydrogen bond provided that at least one of $R_1$ and $R_2$ is a group having an active hydrogen atom capable of forming a hydrogen bond;

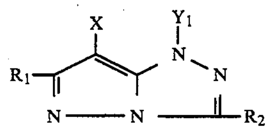

Formula [II]

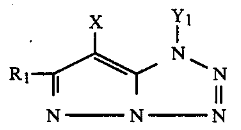

Formula [III]

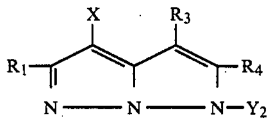

Formula [IV]

-continued

Formula [V]

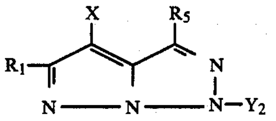

In Formulas [II] through [V], $R_1$ represents a group having an active hydrogen atom capable of forming a hydrogen bond, $R_2$, $R_3$, $R_4$, $R_5$, $Y_1$ and $Y_2$ independently represent a hydrogen atom or a substituent, and X represents a hydrogen atom or a substituent capable of being split off upon reaction with the oxidized product of a color developing agent;

Formula [VI]

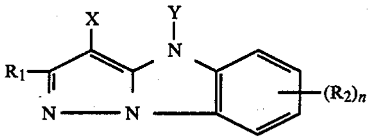

wherein $R_1$ represents a group having an active hydrogen atom capable of forming a hydrogen bond, $R_2$ represents a substituent, n is an integer of from 0 to 4 provided that when n is 2 or more, respective $R_2$'s may be the same with or the different from each other, X represents a hydrogen atom or a substituent capable of being split off upon reaction with the oxidized product of a color developing agent, and Y represents a hydrogen atom or a substituent.

DETAILED DESCRIPTION OF THE INVENTION

Figure 1:
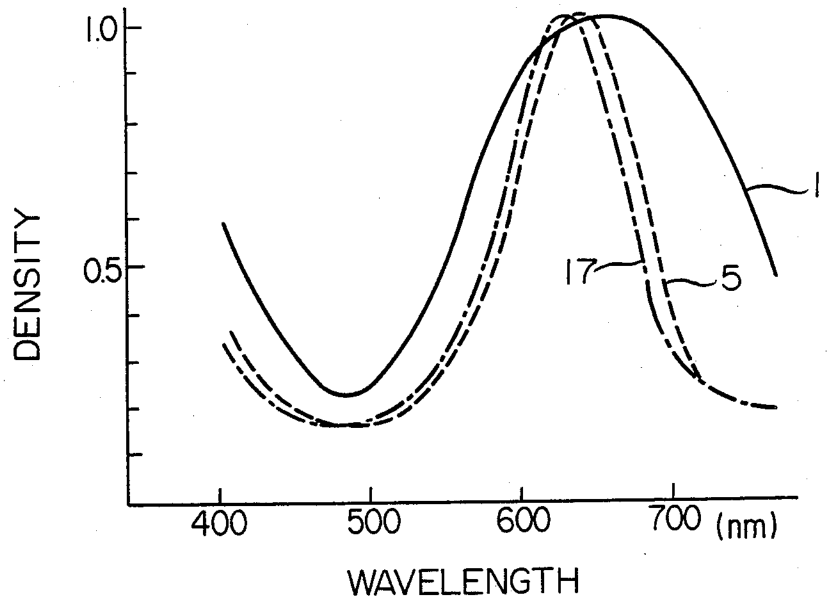
FIG. 1 illustrates the absorption spectra of Samples 1, 5 and 17.

The details of the invention will now be described.

The couplers relating to the invention each represented by the above-given Formula [I] are characterized in that the pyrazolotriazole nucleus thereof contains a group having an active hydrogen atom capable of forming a hydrogen bond (this group will be referred to as 'hydrogen-bondable group'). The hydrogen-bondable group has a an active hydrogen atom which is capable of forming a hydrogen bond with a nitrogen atom in the pyrazolotriazole ring.

The typical examples of the preferable hydrogen-bondable groups each represented by $R_1$ deonted in Formula [I] include the following.

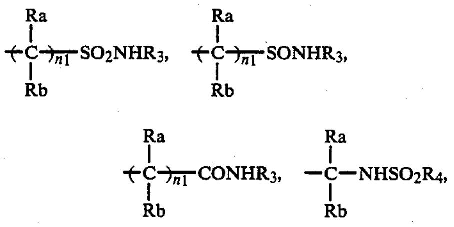

-continued

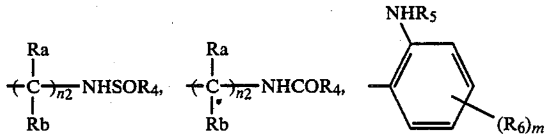

The typical examples of the preferable hydrogen-bondable groups represented by $R_2$ denoted in Formula [I] include the following.

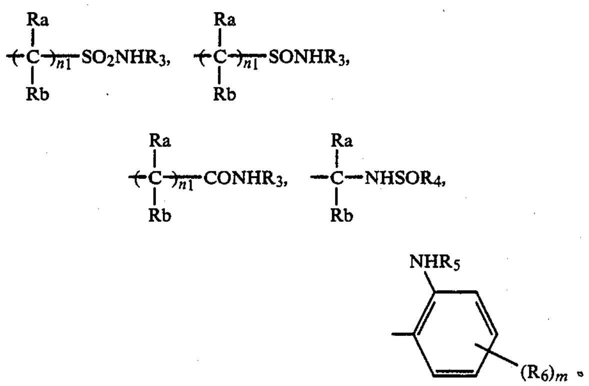

wherein, among the substituents each represented by $R_1$ and $R_2$, Ra, Rb, $R_3$, $R_4$, $R_5$ and $R_6$ each represent a hydrogen atom or a substituent, $n_1$ is an integer of zero or 1, $n_2$ is 1 or 2 and m is any one of 0 through 4, provided that, when m is 2 or more, respective $R_6$ may be the same with or the different from each other.

Ra and Rb each represent a hydrogen atom, an alkyl group, an aryl group, a heterocyclic residual group and so forth;

$R_3$ represents a hydrogen atom, an alkyl group, an aryl group, a heterocyclic residual group and, besides a sulfonyl group, a sulfinyl group, a carbonyl group and so forth;

$R_4$ represents a hydrogen atom, an alkyl group, an aryl group, a heterocyclic residual group and so forth;

$R_5$ represents atom, an alkyl group, an aryl group, a heterocyclic residual group and, besides, a sulfonyl group, a sulfinyl group, a carbonyl group and so forth, and the preferable ones include the sulfonyl group, sulfinyl group and carbonyl group;

$R_6$ represents a hydrogen atom and a substituent, and there is no special limitation to the substituents represented by $R_6$.

The above-given substituents are also allowed to contain a substituent including ballast groups such as a long-chained hydrocarbon group, a polymer residual group, and so forth.

The hydrogen-bondable groups represented by $R_1$ and/or $R_2$, which are used in the invention include, preferably, $—SO_2NHR_3$, $—SONHR_3$, $—CONHR_3$,

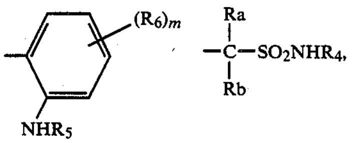

-continued

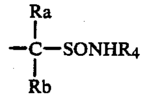 and 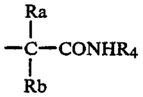

and, among them, further preferable ones are $—SO_2NHR_3$, $—SONHR_3$, $CONHR_3$ and

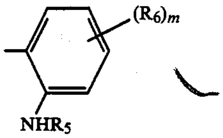

In Formula [I], when $R_1$ or $R_2$ does not represent the above-mentioned hydrogen-bondable substituent but represents others, the $R_1$ or $R_2$ represents a hydrogen atom or a substituent. There is no special limitation to the substituents. The typical examples thereof include each group of alkyl, aryl, anilino, acylamino, sulfonamido, alkylthio, arylthio, alkenyl, cycloalkyl and so forth and, besides, a halogen atom, each group of cycloakenyl, alkinyl, heterocyclic, sulfonyl, sulfinyl, phosphonyl, acyl, cyano, alkoxy, aryloxy, hetercyclic-oxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl and heterocyclic-thio and, in addition, a spiro compound residual group, a cross-linked hydrocarbon compound residual group and so forth.

The alkyl groups represented by $R_1$ and/or $R_2$ preferably include those having 1 to 32 carbon atoms. They may also be straight-chained or branched.

The aryl groups represented by $R_1$ and/or $R_2$ preferably include a phenyl group.

The acylamino groups represented by $R_1$ and/or $R_2$ include, for example, an alkylcarbonylamino group, an arylcarbonylamino group and so forth.

The sulfonamido groups represented by $R_1$ and/or $R_2$ include, for example, an alkysulfonylamino group, an arylsulfonylamino group and so forth.

The alkylthio groups, and the alkyl and aryl components of the arylthio group each represented by $R_1$ and/or $R_2$ include the alkyl group and aryl group each represented by the above-given $R_1$ and/or $R_2$.

The alkenyl groups represented by $R_1$ and/or $R_2$ include, preferably, those having 2 to 32 carbon atoms, the cycloalkyl groups include, preferably, those having 3 to 12 carbon atoms and, more preferably, those having 5 to 7 carbon atoms. The alkenyl groups may be straight-chained or branched.

The cycloalkenyl groups represented by $R_1$ and/or $R_2$ include, preferably, those having 3 to 12 carbon atoms and, more preferably, those having 5 to 7 carbon atoms.

The sulfonyl groups represented by $R_1$ and/or $R_2$ include an alkylsulfonyl group, an arylsulfonyl group and so forth;

The sulfinyl groups include an alkylsulfinyl group, an arylsulfinyl group and so forth;

The phosphonyl groups include an alkylphosphonyl group, an arylphosphonyl group and so forth;

The acyl groups include an alkylcarbonyl group, an arylcarbonyl group and so forth;

The acyloxy groups include an alkylcarbonyloxy group, an arylcarbonyloxy group and so forth;

The carbamoyloxy groups include an alkylcarbamoyloxy group, an arylcarbamoyloxy group and so forth;

The ureido groups include an alkylureido group, an arylureido group and so forth;

The sulfamoylamino groups include an alkylsulfamoylamino group, an arylsulfamoylamino group and so forth;

The heterocyclic groups include, preferably, those having a 5- to 7-membered ring including, typically, a 2-furyl group, a 2-thienyl group, a 2-pyrimidinyl group, a 2-benzothiazolyl group and so forth;

The heterocyclic-oxy groups include, preferably, those having a 5- to 7-membered ring including, for example, a 3,4,5,6-tetrahydropyranyl-2-oxy group, a 1-phenyltetrazole-5-oxy group and so forth;

The heterocyclic-thio groups include, preferably, those having a 5- to 7-membered ring including, for example, a 2-pyridylthio group, a 2-benzothiazolylthio group, a 2,4-diphenoxy-di-1,3-1,3,5-triazole-6-thio group and so forth;

The siloxy groups include, a trimethylsiloxy group, a triethylsiloxy group, a dimethylbutylsiloxy group and so forth;

The imido groups include a succinimido group, a 3-heptadecylsuccinimido group, a phthalimido group, a glutarimido group and so forth;

The spiro compound residual groups include a spiro [3.3] heptane-1-yl and so forth;

The cross-linked hydrocarbon compound residual groups include bicyclo [2.2.1] heptane-1-yl, tricyclo [3.3.1.1$^{37}$] decane-1-yl, 7,7 [2.2.1] heptane-1-yl and so forth;

Besides the above-given groups, the following groups may preferably be used. Namely, such a substituted carbamoyl group as dialkylcarbamoyl, diarylcarbamoyl, alkyl.arylcarbamoyl and so forth and such a substituted sulfamoyl group as dialkylsulfamoyl, diarylsulfamoyl, alkyl.arylsulfamoyl and so forth.

The above-given groups are also allowed to contain a substituent including ballast groups and the like such as a long-chained hydrocarbon group, a polymer residual group and so forth.

In the couplers represented by the aforegiven Formula [I], which relate to this invention, it is particularly preferable that $R_1$ and $R_2$ each represent hydrogen-bondable groups.

Another particularly preferable case is that either one of $R_1$ and $R_2$ represents a hydrogen-bondable group and the other represents an electron withdrawing group. Such electron withdrawing groups should preferably be those having not less than +20 of a substituent constant $\delta p$ which is defined by Hammett. The typical examples of these substituents include each group of sulfonyl, sulfinyl, sulfonyloxy, phosphoryl, pyrrolyl, tetrazolyl, cyano, acyl, acyloxy, carboxyl, oxycarbonyl, nitro and so forth and a halogen atom. Besides the above, the following substituents may also be useful. Namely, each group of N,N-di substituted sulfamoyl, N,N-di substituted carbamoyl, 1-halogenated alkyl, 1-halogenated alkoxy, tetrafluoroaryl, pentafluoroaryl, tetrafluoroaryloxy, pentafluoroaryloxy and so forth. Among the above-given substituents, the particularly preferable electron withdrawing groups include each group of sulfonyl, sulfinyl, sulfonyloxy, sulfamoyl and carbamoyl.

The substituents represented by X, which are capable of splitting off upon reaction with the oxidized product of a color developing agent, include, for example, a halogen atom such as a chlorine atom, a bromine atom, a fluorine atom and so forth and each of the groups including alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring bonded to an N atom, alkyloxycarbonylamino, aryloxycarbonylamino, carboxyl,

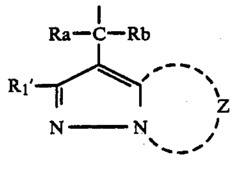

wherein $R_1'$ is synonymous with the aforegiven $R_1$ and/or $R_2$; Ra and Rb each represent a hydrogen atom, an aryl group, an alkyl group or a heterocyclic group; and Z represents a group of non-metal atoms necessary to complete a nitrogen-containing heterocyclic ring; the nitrogen-containing heterocyclic rings include, for example, a pyrazole ring, an imidazole ring, a triazole ring, a tetrazole ring and so forth and, more preferably, a triazole ring that is a part of the structure completing. the couplers represented by Formula [I]. These heterocyclic rings are also allowed to have a substituent. Among them, a halogen atom is preferable. The particularly preferable ones represented by X are a hydrogen atom and a chlorine atom.

In Formula [I], Y represents a hydrogen atom or a substituent. The preferable substituents represented by X include, for example, those capable of releasing from the compound of the invention upon reaction of the compound with the oxidized product of a color developing agent. For example, the substituents represented by Y include a group capable of releasing under an alkaline condition, such as those described in Japanese Patent Publication Open to Public Inspection (Hereinafter called Japanese patent O.P.I. Publication) No. 228444-1986 and so forth, a substituent capable of coupling off upon reaction with the oxidized product of a color developing agent such as those described in Japanese patent O.P.I. Publication No. 133731-1981, and so forth.

Y is preferably a hydrogen atom.

The cyan couplers represented by Formula [I] may be more preferably represented by the following Formula [I'].

Formula [I']

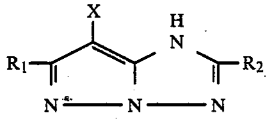

In Formula [I'], $R_1$, $R_2$ and X are synonymous with those denoted in Formula [I].

The typical examples of the compounds of the invention will be given below. It is, however, to be understood that these examples shall be some of the typical examples of the compounds of the invention and the invention shall not be limited thereto.

Formula [I']
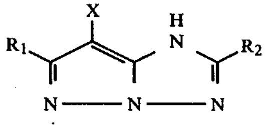
| Compound No. | $R_1$ | $R_2$ | X |
|---|---|---|---|
| I'-1 | 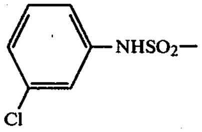 | 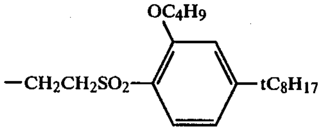 | Cl |
| I'-2 | $C_2H_5NHSO_2-$ | 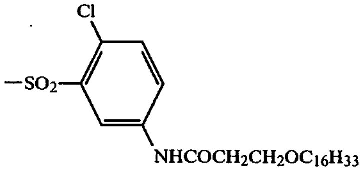 | H |
| I'-3 | 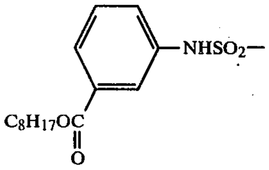 | 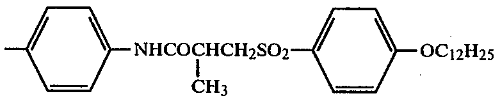 | H |
| I'-4 | $C_2H_5NHSO_2-$ | 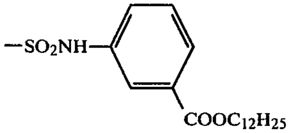 | H |
| I'-5 | 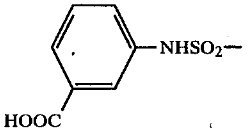 | 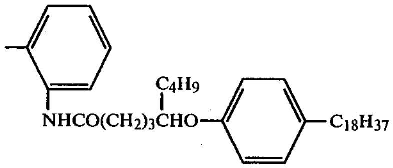 | H |

-continued
Formula [I']
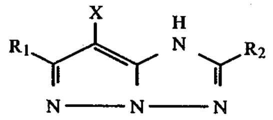
| Compound No. | $R_1$ | $R_2$ | X |
|---|---|---|---|
| I'-6 | (n)$C_4H_9NHSO_2$— | 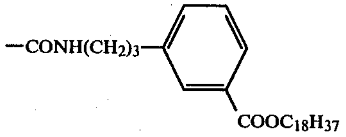 | H |
| I'-7 | 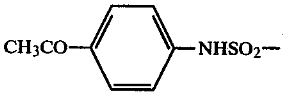 | 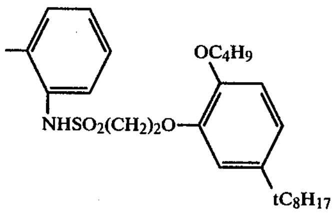 | H |
| I'-8 | (t)$C_4H_9NHSO_2$— | —$SO_2N(C_{12}H_{25})_2$ | —$NHCOCF_3$ |
| I'-9 | $C_3H_7NHSO_2$— | 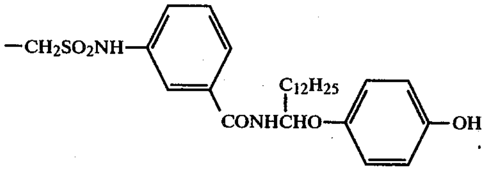 | 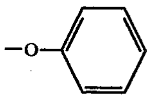 |
| I'-10 | $CH_3NHSO_2$— | —$CH_2CONHC_{11}H_{23}$ | H |
| I'-11 | $C_2H_5NHSO_2$— | 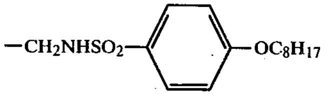 | Cl |
| I'-12 | $C_6H_5NHSO_2$— | —$CH_2CH_2NHCONHC_{18}H_{37}$ | H |
| I'-13 | 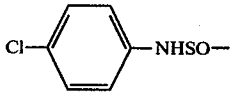 | —$CONHC_{16}H_{33}$ | 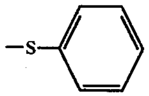 |

-continued
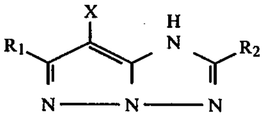
Formula [I']
| Compound No. | $R_1$ | $R_2$ | X |
|---|---|---|---|
| I'-14 | $C_8H_{17}NHSO-$ | 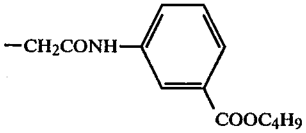 | Cl |
| I'-15 | $CH_3NHCO-$ | 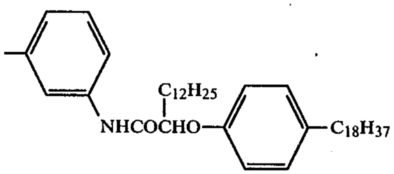 | Br |
| I'-16 | 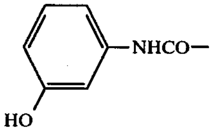 | 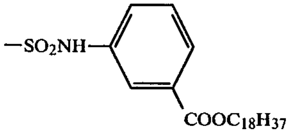 | H |
| I'-17 | $C_6H_{13}NHCO-$ | 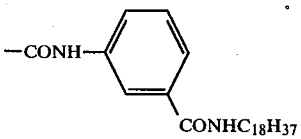 | H |
| I'-18 | $C_2H_5NHCO-$ | 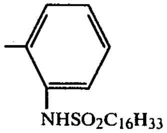 | H |

-continued
Formula [I']
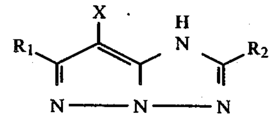
| Compound No. | $R_1$ | $R_2$ | X |
|---|---|---|---|
| I'-19 | $C_{10}H_{21}NHCO-$ | 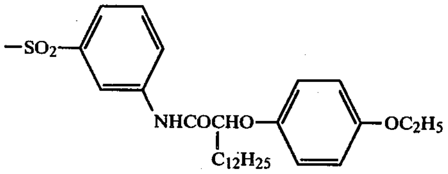 | 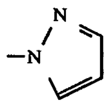 |
| I'-20 | 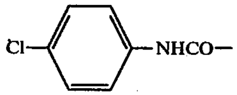 | 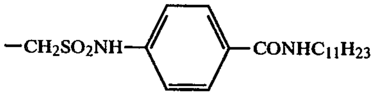 | Cl |
| I'-21 | $C_2H_5NHCO-$ | 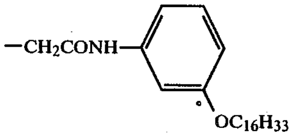 | H |
| I'-22 | $C_3H_7NHCO-$ | $-CH_2NHSOC_{16}H_{33}$ | $-SC_8H_{17}$ |
| I'-23 | 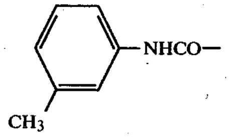 | 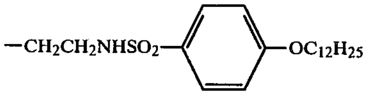 | Cl |
| I'-24 | $CH_3NHSO_2CH_2-$ | 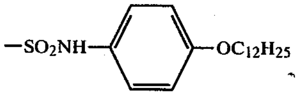 | Cl |

-continued
Formula [I']
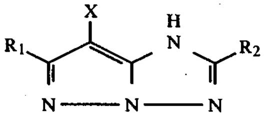
| Compound No. | $R_1$ | $R_2$ | X |
|---|---|---|---|
| I'-25 | $C_4H_9NHSO_2CH_2-$ | 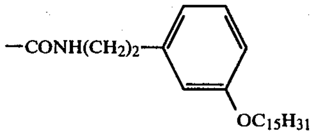 | H |
| I'-26 | $C_6H_5NHSO_2CH_2-$ | 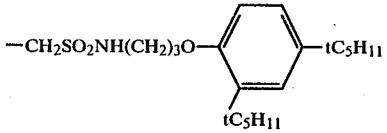 | Cl |
| I'-27 | $C_2H_5NHSO_2CH_2-$ | 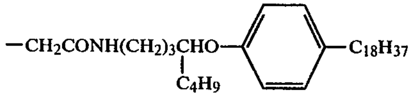 | Cl |
| I'-28 | 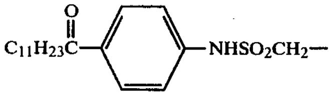 | 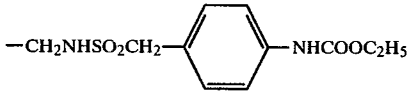 | 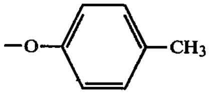 |
| I'-29 | $C_3H_7NHSO_2CH_2-$ | $-CH_2CH_2NHSO_2C_{12}H_{25}$ | 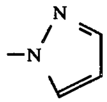 |
| I'-30 | $C_2H_5NHSO_2CH_2-$ | 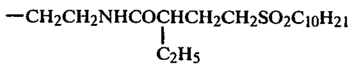 | Cl |
| I'-31 | 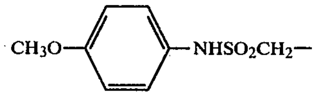 | 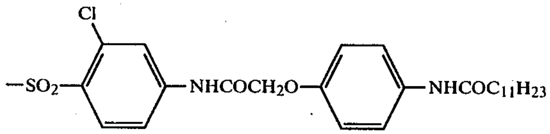 | H |

-continued
Formula [I']
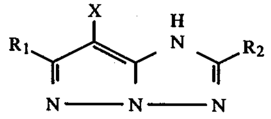
| Compound No. | $R_1$ | $R_2$ | X |
| --- | --- | --- | --- |
| I'-32 | $C_{11}H_{23}NHSO_2CH_2-$ | 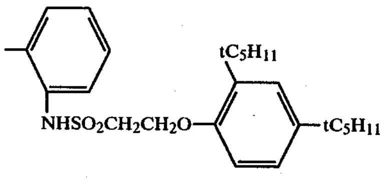 | Cl |
| I'-33 | $C_8H_{17}NHSOCH_2-$ | 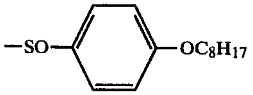 | H |
| I'-34 | $C_6H_5NHSOCH_2-$ | $-CONHC_{18}H_{37}$ | H |
| I'-35 | $C_2H_5NHSOCH_2-$ | 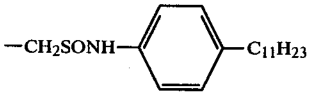 | Cl |
| I'-36 | $CH_3NHCOCH_2-$ | 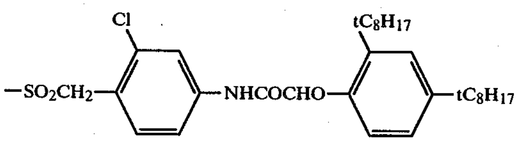 | Cl |
| I'-37 | $C_{11}H_{23}NHCOCH_2-$ | 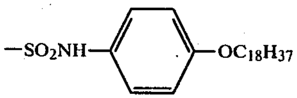 | 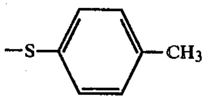 |
| I'-38 | $C_6H_5NHCOCH_2-$ | 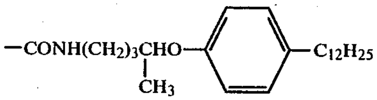 | Cl |

-continued
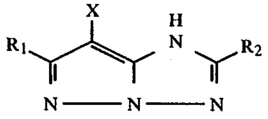
Formula [I']
| Compound No. | $R_1$ | $R_2$ | X |
|---|---|---|---|
| I'-39 | 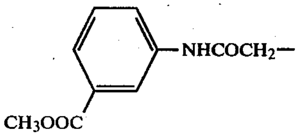 | 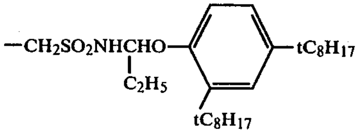 | Cl |
| I'-40 | $C_2H_5NHCOCH_2$— | —$CH_2CONHC_{12}H_{25}$ | Cl |
| I'-41 | $C_4H_9NHCOCH_2$— | 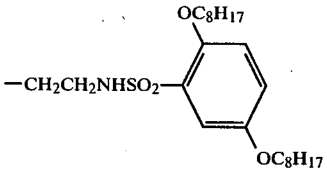 | H |
| I'-42 | $C_2H_5NHCOCH_2$— | 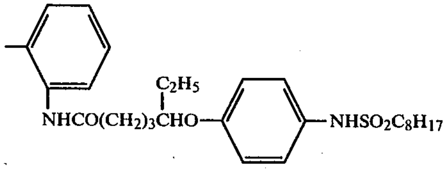 | Cl |
| I'-43 | $C_6H_5CH_2SO_2NHCH_2$— | 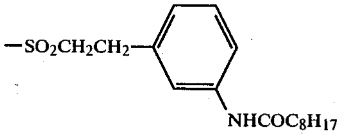 | 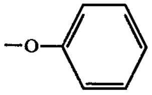 |
| I'-44 | $C_3H_7SO_2NHCH_2$— | —$SO_2NHC_{11}H_{23}$ | Cl |
| I'-45 | $C_4H_9SO_2NHCH_2$— | 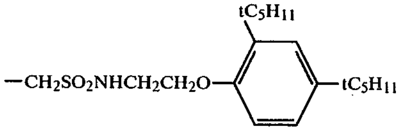 | Cl |

-continued
Formula [I']
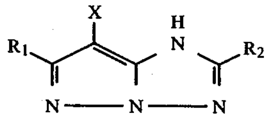
| Compound No. | $R_1$ | $R_2$ | X |
|---|---|---|---|
| I'-46 | 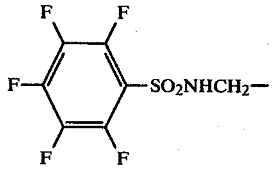 | 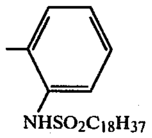 | Cl |
| I'-47 | 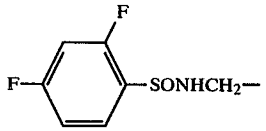 | 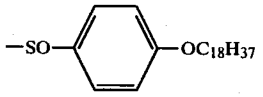 | H |
| I'-48 | $C_2H_5SONHCH_2$— | 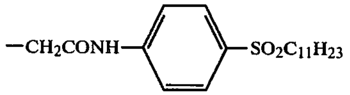 | Cl |
| I'-49 | 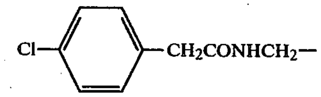 | 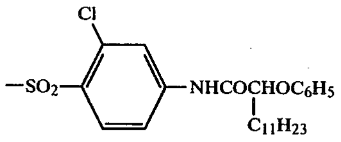 | Cl |
| I'-50 | $C_4H_9CONHCH_2$— | 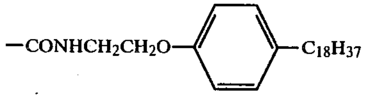 | Cl |
| I'-51 | $CH_3CONHCH_2$— | 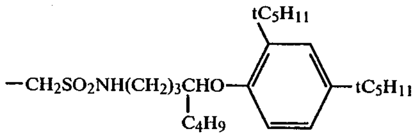 | Cl |

-continued
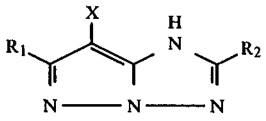
Formula [I']
| Compound No. | $R_1$ | $R_2$ | X |
|---|---|---|---|
| I'-52 | $C_4H_9SONHCH_2CH_2-$ | 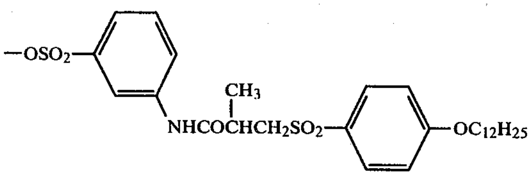 | Cl |
| I'-53 | $C_2H_5SONHCH_2CH_2-$ | $-SONHC_{18}H_{37}$ | Cl |
| I'-54 | 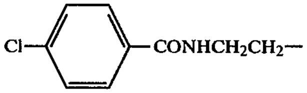 | 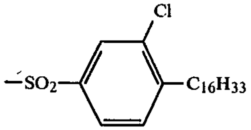 | $-NHSO_2C_6H_5$ |
| I'-55 | $CF_3CONHCH_2CH_2-$ | 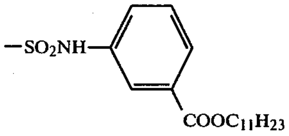 | H |
| I'-56 | $C_4H_9CONHCH_2CH_2-$ | 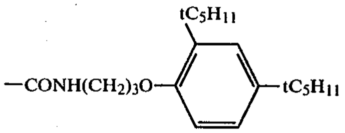 | Cl |
| I'-57 | $C_3H_7CONHCH_2CH_2-$ | 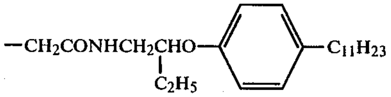 | Cl |

-continued
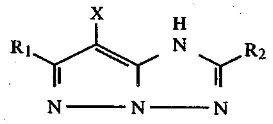
Formula [I']
| Compound No. | $R_1$ | $R_2$ | X |
| --- | --- | --- | --- |
| I'-58 | $C_{11}H_{23}CONHCH_2CH_2-$ | 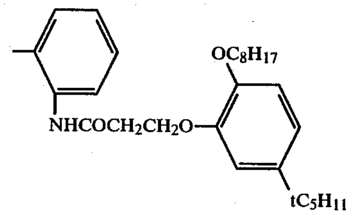 | H |
| I'-59 | $C_6H_5CONHCH_2CH_2-$ | $-CH_2CH_2NHSO_2C_{18}H_{37}$ | Cl |
| I'-60 | 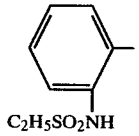 | 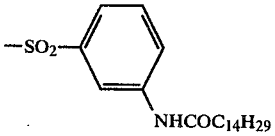 | Cl |
| I'-61 | 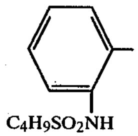 | 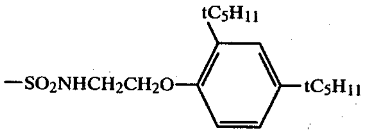 | Cl |
| I'-62 | 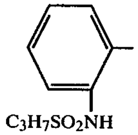 | 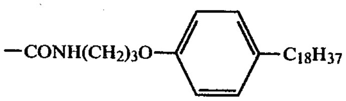 | 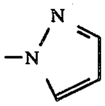 |
| I'-63 | 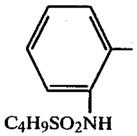 | 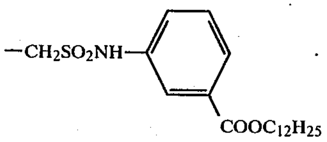 | Cl |

-continued
Formula [I']
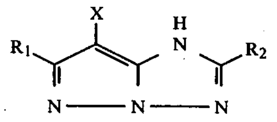
| Compound No. | $R_1$ | $R_2$ | X |
| --- | --- | --- | --- |
| I'-64 | 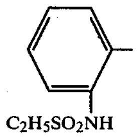 | 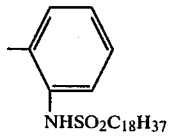 | H |
| I'-65 | 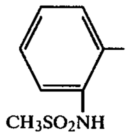 | 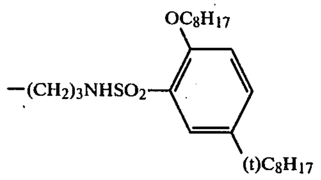 | Cl |
| I'-66 | 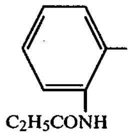 | 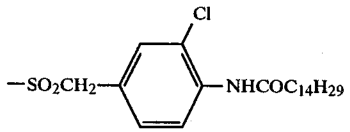 | Br |
| I'-67 | 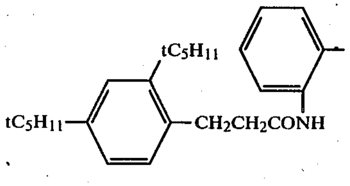 | 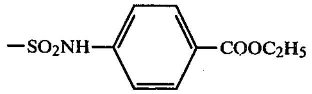 | Cl |
| I'-68 | 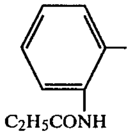 | 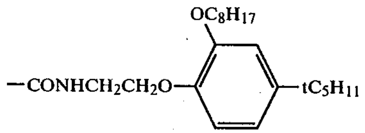 | Cl |

-continued
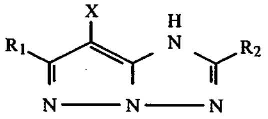
Formula [I']
| Compound No. | $R_1$ | $R_2$ | X |
| --- | --- | --- | --- |
| I'-69 | $CH_3$— | 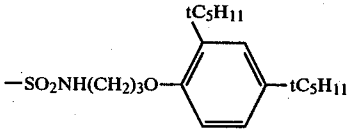 | Cl |
| I'-70 | $C_4H_9$— | 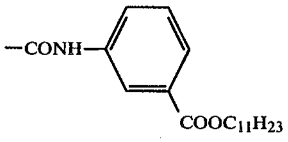 | Cl |
| I'-71 | $CH_3$— | 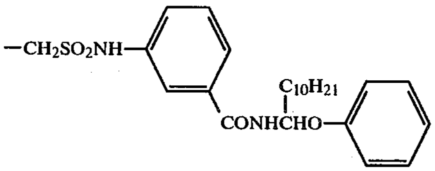 | Cl |
| I'-72 | 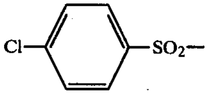 | 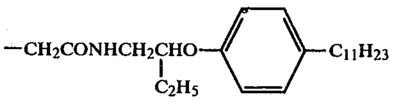 | Cl |
| I'-73 | $CH_3SO_2NHCH_2CH_2$— | 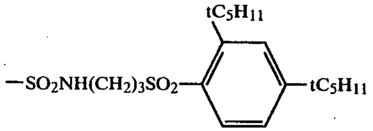 | Cl |
| I'-74 | 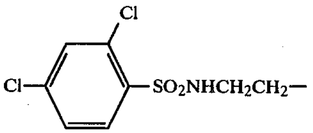 | 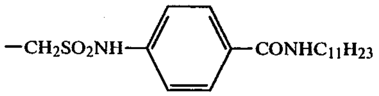 | 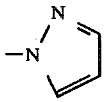 |

-continued
Formula [I']
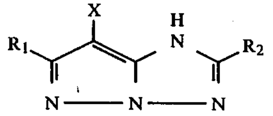
| Compound No. | $R_1$ | $R_2$ | X |
| --- | --- | --- | --- |
| I'-75 | 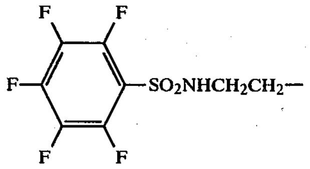 | 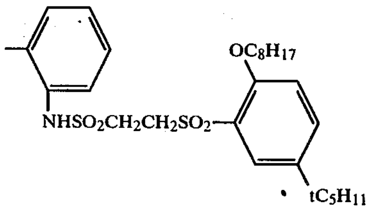 | Cl |
| I'-76 | $C_6H_5SO_2$— | 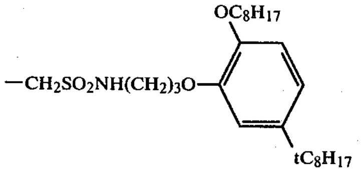 | Cl |
| I'-77 | $CH_3SO_2$— | 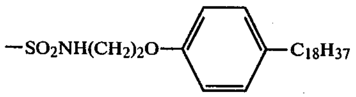 | H |
| I'-78 | 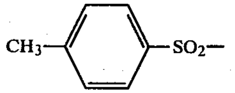 | 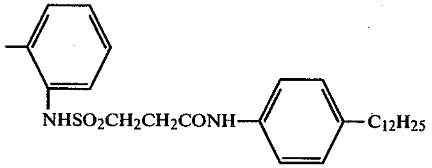 | H |

The cyan couplers represented by Formula [I] may readily be prepared with reference to Japanese Patent O.P.I. Publication Nos. 171,956-1984, 172,982-1985, 190,779-1985, 197,688-1985, 215,687-1985 and 65247-1986, an so forth.

Typical synthesis examples will be given below.

SYNTHESIS EXAMPLE 1 (SYNTHESIS OF COMPOUND 18)

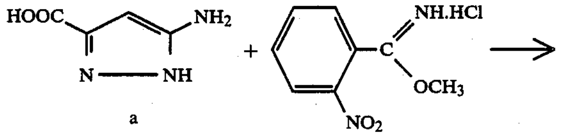

a b

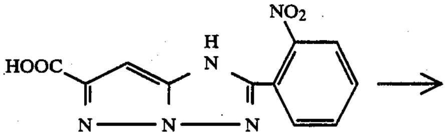

c

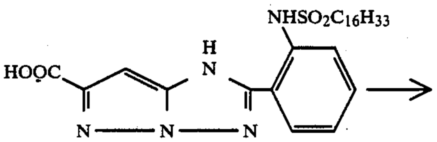

Compound 18 d

[Synthesis of c]

Following an ordinary process, 3-carboxy-5-aminopyrazole a was synthesized. Both of imidochloride b and a were reacted together in an ordinary process, so that c was synthesized.

[c→d]

c of 0.10 mols was dissolved in 400 ml of THF and the resulted solution was hydrogenated with Pd/C. After the Pd/C was filtrated and the solvent was then distilled off. The resulted crystals were dissolved in 200 ml of acetonitrile and 0.11 mols of hexadecanesulfonyl chloride were then added. Triethylamine of 0.12 mols were dropped into the resulted solution. After the solution was stirred for two hours at room temperature, the solution was concentrated to be one third. The resulted crystals were filtrated and recrystallized with ethyl acetate, so as to obtain 0.043 mols of d.

[d→Compound 18]

A mixed solution of triphenylphosphine of 0.050 mols, carbon tetrachloride of 100 ml and THF of 200 ml was refluxed for 30 minutes with heating and was then cooled down to 5° C. After then, 0.043 mols of d were added and was then stirred for 30 minutes. Thereafter, 0.090 mols of ethylamine were added and a reflux was made for one hour with heating.

Insoluble matters were filtrated and the solvent was distilled off. The resulted residues were recrystallized with acetonitrile, so that 0.018 mols of a crystallized compound in a white powder form.

SYNTHESIS EXAMPLE 2 (SYNTHESIS OF COMPOUND NO. 4)

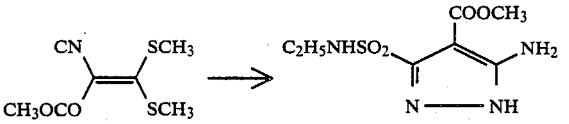

a b

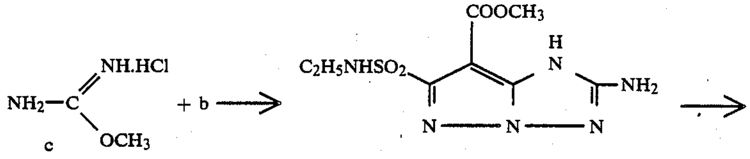

c d

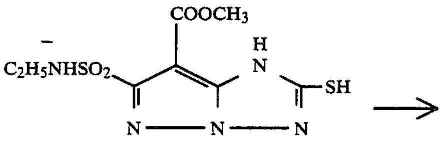

e

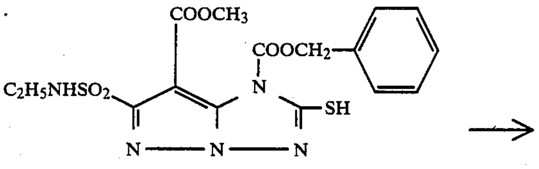

f

-continued

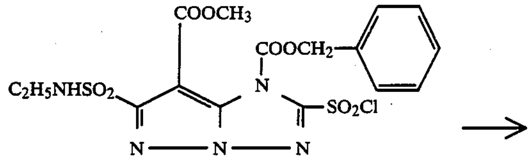

g

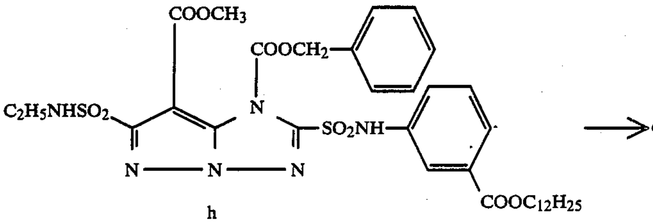

h

Compound No. 4

[a→b]

a of 0.5 mols and sodium ethylaminosulfinate of 1.1 mols were dissolved in 2 liters of methanol and the resulted solution was refluxed for 4.5 hours with heating. After the solution was distilled off, the resulted residues were added to 3 liters of ethanol and, thereinto 0.5 mols of 100% hydrazine hydrate were dropped. After a reflux was made for 8 hours with heating, the solvent was distilled off and the resulted residues were recrystallized with ethyl acetate, so that 0.205 mols of b were obtained.

[Synthesis of c]

Chloric acid gas of 50 g was blown in a solution of 0.500 mols of cyanamide, 50 g of methanol and 150 ml of dioxane and the reacted mixture was then allowed to stand overnight in a refrigerator at 5° C. The deposited crystals were filtrated and were then washed with ethyl ether, so that 0.250 mols of c were obtained.

[Synthesis of d]

In 400 ml of toluene, b of 0.205 mols and c of 0.226 mols were refluxed with heating for 20 hours. Toluene was then distilled off and the residues were dissolved in 400 ml of ethanol. The resulted solution was added at 0° C. with a methanol solution containing 0.225 mols of hydroxylamine and was then stirred for 2 hours at room temperature. The resulted reacted solution was poured into 2 liters of water to filtrate a deposition. Further, the deposition was dissolved in 1 liter of THF and thereinto 0.085 mols of triethylamine were added and stirred. Into the resulted solution, a THF solution containing 15.0 g of p-toluenesulfonic acid chloride was dropped and stirred. Then, the resulted insoluble matters were filtrated and the filtrate was refluxed for 7 hours with heating under a nitrogen flow. The solvent was distilled off and the residues were washed with a small amount of cooled methanol, so that 0.100 mols of d were obtained.

[d→e]

d of 0.100 mols were added into a reaction solution containing 25 ml of hydrochloric acid and 25 g of ice. Further, into the resulted solution with keeping a temperature at 0° C., 0.110 mols of an aqueous sodium nitrite solution were gradually added at a temperature of not higher than 5° C. The resulted solution was gradually added into 25 ml of an aqueous solution containing 19 g of potassium ethylxanthate which was warmed up to 40° C., and stirred for 30 minutes at 45° C. The resulted reacted solution was extracted with ethyl acetate and the extractive was washed with an aqueous 10% sodium hydroxide solution and water. After the solvent was distilled off, 100 ml of 95% ethanol and 24 g of potassium hydroxide were added and the resulted solution was then refluxed for 5 hours with heating.

After the solvent was distilled off and th remained aqueous layer was acidified with sulfuric acid, an extraction was made with ethyl acetate and the solvent was distilled off, so that 0.050 mols of e that was a oily crude product were obtained.

[e→f]

The oily crude product of e of 0.050 mols and a 2N aqueous hydroxide solution of 30 ml were mixed in acetonitrile while cooling with ice and stirring. Benzyloxycarbonyl chloride of 0.050 mols and a 2N aqueous solution of sodium hydroxide of 15.5 ml were gradually dropped into the resulted mixture and were then stirred for one hour.

After the mixture was neutralized with hydrochloric acid and was cooled, a deposition was filtrated and then washed. The resulted matter was recrystallized with ethyl acetate, so that 0.040 mols of f were obtained.

[f→d]

In 125 ml of water, 0.040 mols of f werer suspended and hydrochloric acid gas was blown thereinto while cooling with ice. The resulted matter was then stirred for 30 minutes. The excessive amount of hydrochloric acid gas was removed and an extraction was made with ethyl acetate. After the extraction was washed with an aqueous sodium hydrogensulfite solution and an aqueous sodium hydrogencarbonate solution, the solvent was then distilled off, so that 0.020 moles of crude crystals of g were obtained.

[g→h]

An acetonitrile solution of 100 ml containing 0.020 moles of crude crystals of g were added with 0.020 mols of m-dodecaoxycarbonylphenylamine. Further, 0.020 mols of pyridine was added thereto and stirred for one hour. After the resulted matter was still further stirred for another one hour at 50° C. and was then poured into 500 ml of water. The deposition was filtrated, so that 0.009 mols of a crude product h were obtained.

[h→Compound No. 4]

h of 0.009 mols were dissolved in 130 ml of THF and the solution was reduced with Pd/C. After the Pd/C was removed and the solvent was then distilled off. The resulted deposition was added into a mixed solvent of 40 ml of acetic acid, 11 ml of sulfuric acid and 1.2 ml of water, and the solution was reduced for 2 hours with heating.

After the reduced matter was neutralized with an aqueous sodium hydroxide solution, an extraction was made with ethyl acetate and concentration was then made. After the concentration was added with water, the resulted deposition was filtrated therefrom and was then recrystallized with acetonitrile, so that 0.003 mols of white powdered crystals, Compound No. 4, were obtained.

The couplers relating to the invention each represented by the above-given Formulas [II], [III], [IV] and [V] are characterized in that at least $R_1$ of the pyrazoloazole nucleus thereof contains a hydrogen-bondable group. The hydrogen-bondable group has an active hydrogen atom which is capable of forming a hydrogen bond with a nitrogen atom in the pyrazoloazole ring.

The typical examples of the preferable hydrogen-bondable groups each represented by at least $R_1$ include the following.

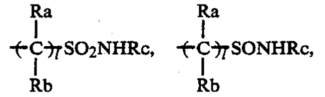

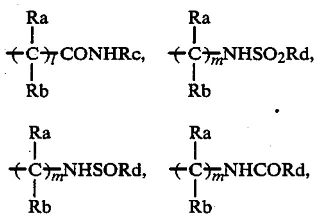

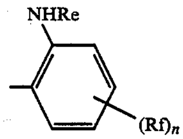

wherein Ra, Rb, Rc, Rd, Re and Rf each represent a hydrogen atom or a substituent, l is an integer of zero or 1, m is 1 or 2 and n is an integer of 0 through 4, provided that, when n is 2 or more, respective Rf's may be the same with or the different from each other.

Ra and Rb each represent a hydrogen atom, an alkyl group, an aryl group, a heterocyclic residual group and so forth;

Rc represents a hydrogen atom, an alkyl group, an aryl group, a heterocyclic residual group and, besides, sulfonyl group, a sulfinyl group, a carbonyl group and so forth;

Rd represents a hydrogen atom, an alkyl group, an aryl group, a heterocyclic residual group and so forth;

Re represents a hydrogen atom, an alkyl group, an aryl group, a heterocyclic residual group and, besides, a sulfonyl group, a sulfinyl group, a carbonyl group and so forth, and the preferable ones include the sulfonyl group, sulfinyl group and carbonyl group;

Rf represents a hydrogen atom and a substituent, and there is no special limitation to the substituents represented by Rf.

The above-given substituents are also allowed to contain a substituent including ballast groups such as a long-chained hydrocarbon group, a polymer residual group, and so forth.

In the invention, the hydrogen-bondable groups represented by $R_1$ include, preferably,

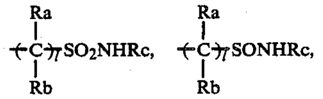

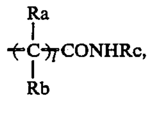 and 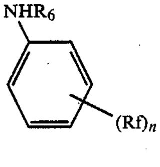

and, among them, furthr preferable ones are $-SO_2NHRc$, $-SONHRc$, $-CONHRc$ and

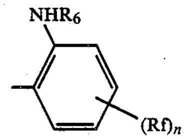

In Formulas [II], [III], [IV] and [V], $R_2$, $R_3$, $R_4$ and $R_5$ may be either the above-mentioned hydrogen-bondable group or the other substituent and a hydrogen atom.

There is no special limitation to the substituents represented by $R_2$, $R_3$, $R_4$ and $R_5$. The typical examples thereof include each group of alkyl, aryl, anilino, acylamino, sulfonamido, alkylthio, arylthio, alkenyl, cycloalkyl and so forth and, besides, a halogen atom, each group of cycloalkenyl, alkinyl, heterocyclic, sulfonyl, sulfinyl, phosphonyl, acyl, carbamoylsulfamoyl, cyano, alkoxy, aryloxy, hetercyclic-oxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl and heterocyclic-thio and, in addition, a spiro compound residual group, a cross-linked hydrocarbon compound residual group and so forth.

The alkyl groups represented by $R_2$ through $R_5$ preferably include those having 1 to 32 carbon atoms. They may also be straight-chained or branched.

The aryl groups represented by $R_2$ through $R_5$ preferably include a phenyl group.

The acylamino groups represented by $R_2$ through $R_5$ include an alkylcarbonylamino group, an arylcarbonylamino group and so forth.

The sulfonamido groups represented by $R_2$ through $R_5$ include an alkylsulfonymlamino group, an arylsulfonylamino group and so forth.

The alkylthio groups, and the alkyl and aryl components of the arylthio group each represented by $R_2$ through $R_5$ include the alkyl group and aryl group each represented by the above-given R.

The alkenyl groups represented by $R_2$ through $R_5$ include, preferably, those having 2 to 32 carbon atoms, the cycloalkyl groups include, preferably, those having 3 to 12 carbon atoms and, more preferably, those having 5 to 7 carbon atoms. The alkenyl groups may be straight-chained or branched.

The cycloalkenyl groups represented by $R_2$ through $R_5$ include, preferably, those having 3 to 12 carbon atoms and, more preferably, those having 5 to 7 carbon atoms.

The sulfonyl groups represented by $R_2$ through $R_5$ include an alkylsulfonyl group, an arylsulfonyl group and so forth;

The sulfinyl groups include an alkylsulfinyl group, an arylsulfinyl group and so forth;

The phosphonyl groups include an alkylphosphonyl group, an alkoxyphosphonyl group, an aryloxyphosphonyl group, an arylphosphonyl group and so forth;

The acyl groups include an alkylcarbonyl group, an arylcarbonyl group and so forth;

The carbamoyl groups include an alkylcarbamoyl group, an arylcarbamoyl group and so forth;

The sulfamoyl groups include an alkylsulfamoyl group, an arylsulfamoyl group and so forth;

The acyloxy groups include an alkylcarbonyloxy group, an arylcarbonyloxy group and so forth;

The carbamoyloxy groups include an alkylcarbamoyloxy group, an arylcarbamoyloxy group and so forth;

The ureido groups include an alkylureido group, an arylureido group and so forth;

The sulfamoylamino groups include an alkylsulfamoylamino group, an arylsulfamoylamino group and so forth;

The heterocyclic groups include, preferably, those having a 5- to 7-membered ring including, typically, a 2-furyl group, a 2-thienyl group, a 2-pyrimidinyl group, a 2-benzothiazolyl group and so forth;

The heterocyclic-oxy groups include, preferably, those having a 5- to 7-membered ring including for example, a 3,4,5,6-tetrahydropyranyl-2-oxy group, a 1-phenyltetrazole-5-oxy group and so forth;

The heterocyclic-thio groups include, preferably those having a 5- to 7-membered ring including, for example, a 2-pyridylthio group, a 2-benzothiazolythio group, a 2,4-diphenoxy-di-1,3,-1,3,5-triazole-6-thio group and so forth;

The siloxy groups include, a trimethylsiloxy group, a triethylsiloxy group, a dimethylbutylsiloxy group and so forth.

The imido groups include a succinimido group, a 3-heptadecylsuccinimido group, a phthalimido group, a glutarimido group and so forth;

The spiro compound residual groups include a spiro [3.3] heptane-1-yl and so forth;

The cross-linked hydrocarbon compound residual groups include bicyclo [2.2.1] heptane-1-yl, tricyclo [$3.3.1.1^{3\ 7}$] decane-1-yl, 7,7 [2.2.1] heptane-1-yl and so forth;

The above-given groups are also allowed to contain a substituent including ballast groups and the like such as a long-chained hydrocarbon group, a polymer residual group and so forth.

The the cyan couplers represented by the aforegiven Formulas [II], [III], [IV] and [V], which relate to this invention, it is particularly preferable that $R_2$, $R_3$, $R_4$ and $R_5$ each represent electron withdrawing groups. Such electron withdrawing groups should preferably be those having not less than +20 of a substituent constant δp which is defined by Hammett. The typical examples of these substituents include each group of sulfonyl, sulfinyl, sulfonyloxy, sulfamoyl, carbamoyl, phosphoryl, pyrrolyl, tetrazolyl, cyano, acyl, acyloxy, carboxyl, oxycarbonyl, nitro and so forth and a halogen atom. Besides the above, the following groups are also useful, namely, each of the groups of 1-halogenated alkyl, 1-halogenated alkoxy, tetrafluoroaryl, pentafluoroaryl, tetrafluoroaryloxy, pentafluoroaryloxy and so forth. Among the above-given substituents, the particularly preferable electron withdrawing groups include each group of sulfonyl, sulfinyl, sulfonyloxy, sulfamoyl and carbamoyl.

The substituents represented by X, which are capable of splitting off upon reaction with the oxidized product of a color developing agent, include, for example, a halogen atom such as a chlorine atom, a bromine atom, a fluorine atom and so forth and each of the groups including alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring bonded to an N atom, alkyloxycarbonylamino, aryloxycarbonylaimino, carboxyl,

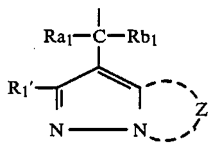

wherein $R_1'$ is synonymous with the aforegiven $R_1$ and/or $R_2$; $Ra_1$ and $Rb_1$ each represent a hydrogen atom, an aryl group, an alkyl group or a heterocyclic group; and Z represents a group of non-metal atoms necessary to complete a nitrogen-containing heterocyclic ring; the nitrogen-containing heterocyclic rings include, for example, a pyrazole ring, a imidazole ring, a triazole ring, a tetra-azole ring and so forth which may have a substituent and, more preferably, a halogen atom. Among them, the particularly preferable one represented by X are a hydrogen atom and a chlorine atom.

In Formulas [II] and [III], $Y_1$ represents a hydrogen atom or a substituent. The preferable substituents represented by $Y_1$ include, for example, those capable of releasing from the compound of the invention upon reaction of the compound with the oxidized product of a color developing agent. For example, the substituents represented by $Y_1$ include a group capable of releasing under an alkaline condition, such as those described in Japanese Patent Publication Open to Public Inspection (Hereinafter called Japanese Patent O.P.I. Publication) No. 228444-1986 and so forth, a substituent capable of coupling off upon reaction with the oxidized product of a color developing agent such as those described in Japanese Patent O.P.I. Publicaton No. 133734-1981, and so forth. $Y_1$ is preferably a hydrogen atom.

In Formulas [IV] and [V], $Y_2$ represents a hydrogen atom or a substituent and, more preferably, a hydrogen atom.

The couplers represented by Formulas [II], [III], [IV] and [V] may be more preferably represented by the following Formulas [II'], [III'], [IV'] and [V'], respectively.

-continued

Formula [II']

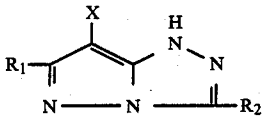

Formula [III']

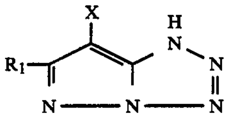

Formula [IV']

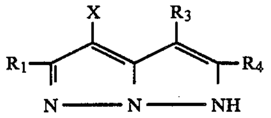

Formula [V']

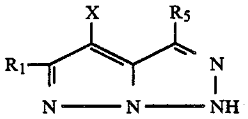

In Formulas [II'], [III'], [IV'] and [V'], $R_1$, $R_2$, $R_3$, $R_4$, $R_5$ and X are synonymous with those denoted in Formulas [II], [III], [IV] and [V], respectively.

The typical examples of the compounds of the invention will be given below. It is, however, to be understood that these examples shall be some of the typical examples of the compounds of the invention and the invention shall not be limited thereto.

Formula [II']
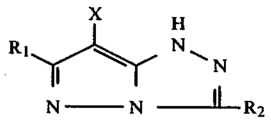
| Compound No. | $R_1$ | $R_2$ | X |
| --- | --- | --- | --- |
| II'-1 | $tC_4H_9NHSO_2-$ | 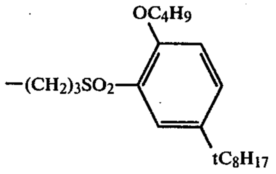 | H |
| II'-2 | $C_2H_5NHSO_2-$ | 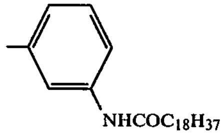 | H |
| II'-3 | 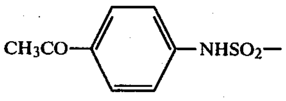 | 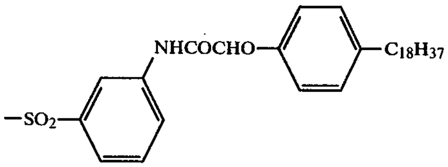 | H |
| II'-4 | 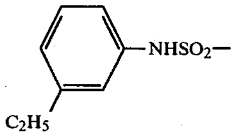 | 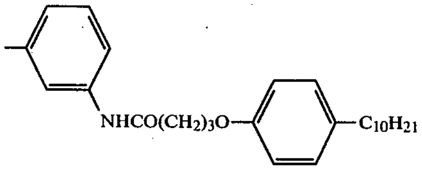 | Cl |
| II'-5 | $CH_3NHSO_2-$ | $-SO_2N(C_{12}H_{25})_2$ | H |

-continued
Formula [II']
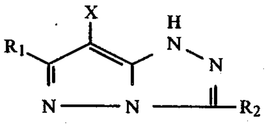
| Compound No. | $R_1$ | $R_2$ | X |
| --- | --- | --- | --- |
| II'-6 | 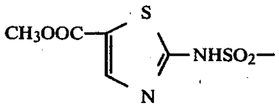 | 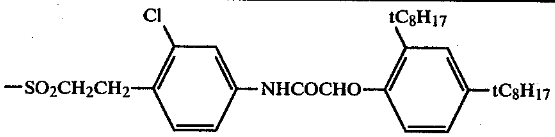 | H |
| II'-7 | 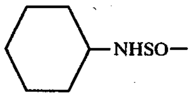 | 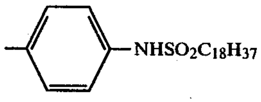 | H |
| II'-8 | $C_2H_5NHCO$— | 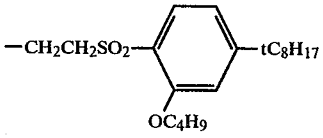 | Br |
| II'-9 | 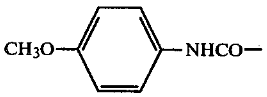 | 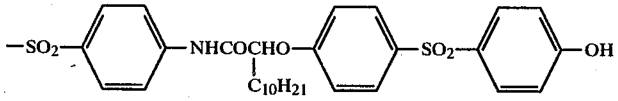 | H |
| II'-10 | (n)$C_4H_9NHCO$— | 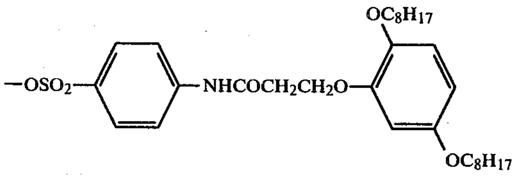 | H |
| II'-11 | (n)$C_{10}H_{21}NHCO$— | 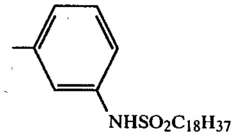 | H |

-continued
Formula [II']
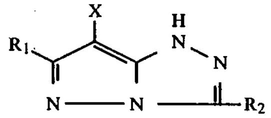
| Compound No. | $R_1$ | $R_2$ | X |
|---|---|---|---|
| II'-12 | $C_3H_7NHSO_2CH_2-$ | 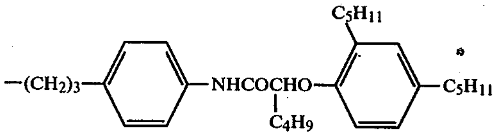 | Cl |
| II'-13 | 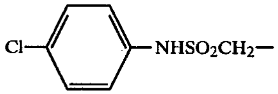 | 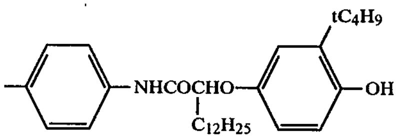 | Cl |
| II'-14 | $C_8H_{17}NHSO_2CH_2-$ | 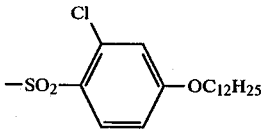 | H |
| II'-15 | $C_2H_5NHSO_2CH_2-$ | 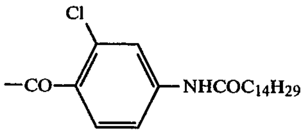 | Cl |
| II'-16 | $C_6H_5NHSOCH_2-$ | 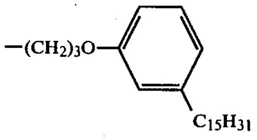 | H |
| II'-17 | $C_4H_9NHCOCH_2-$ | $-\underset{CH_3}{CH}CH_2CH_2SO_2C_{18}H_{37}$ | 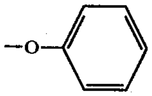 |

-continued
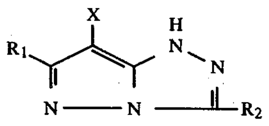
Formula [II']
| Compound No. | $R_1$ | $R_2$ | X |
|---|---|---|---|
| II'-18 | $CH_3NHCOCH_2-$ | 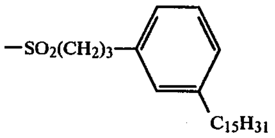 | H |
| II'-19 | $C_{10}H_{21}NHCOCH_2-$ | $-CON(C_6H_{13})_2$ | Cl |
| II'-20 | $C_6H_5SO_2NHCH_2-$ | $-CH(CH_3)CH_2SO_2C_{18}H_{37}$ | H |
| II'-21 | $C_6H_5CH_2SO_2NHCH_2-$ | $-SO_2C_{16}H_{33}$ | 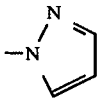 |
| II'-22 | $CH_3SO_2NHCH_2-$ | 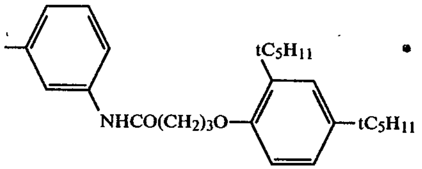 | H |
| II'-23 | $C_2H_5CONHCH_2-$ | 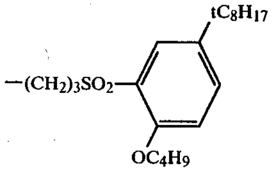 | H |

-continued
Formula [II']
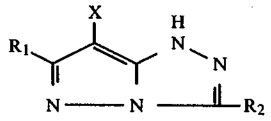
| Compound No. | $R_1$ | $R_2$ | X |
| --- | --- | --- | --- |
| II'-24 | $CH_3CONHCH_2-$ | $-CONH(C_{12}H_{25})$ | 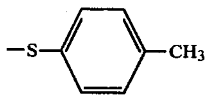 |
| II'-25 | $C_6H_5SO_2NHCH_2CH_2-$ | 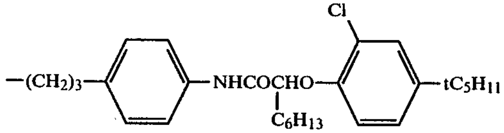 | Cl |
| II'-26 | $CH_3SO_2NHCH_2CH_2-$ | 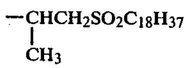 | H |
| II'-27 | 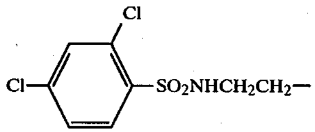 | 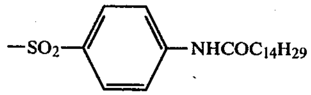 | Cl |
| II'-28 | 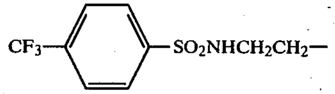 | $-SO_2N(C_8H_{17})_2$ | Cl |
| II'-29 | 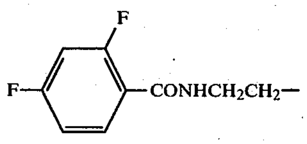 | 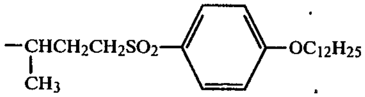 | Cl |

-continued
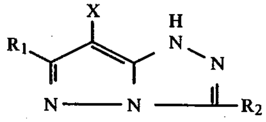
Formula [II']
| Compound No. | $R_1$ | $R_2$ | X |
| --- | --- | --- | --- |
| II'-30 | $C_6H_5CONHCH_2CH_2-$ | 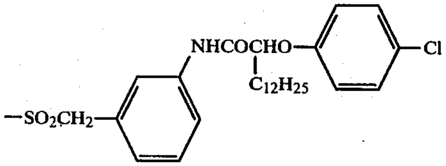 | Cl |
| II'-31 | $CH_3CONHCH_2CH_2-$ | 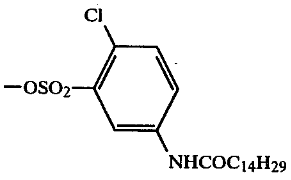 | H |
| II'-32 | 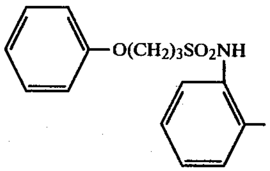 | $-SO_2N(C_{11}H_{23})_2$ | H |
| II'-33 | 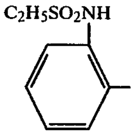 | 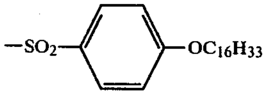 | Cl |
| II'-34 | 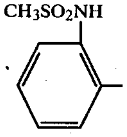 | 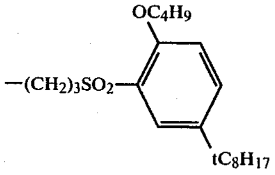 | Cl |

-continued
Formula [II']
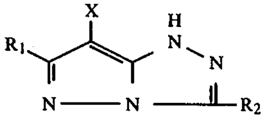
| Compound No. | $R_1$ | $R_2$ | X |
|---|---|---|---|
| II'-35 | 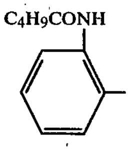 | 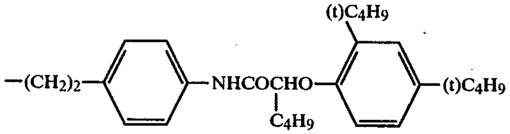 | Cl |
| II'-36 | 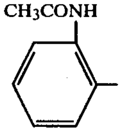 | 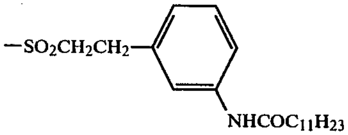 | Cl |

Formula [III']
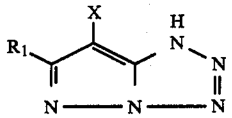
| Compound No. | $R_1$ | X |
|---|---|---|
| III'-1 | 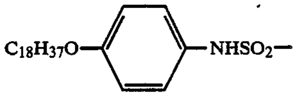 | H |
| III'-2 | $C_{16}H_{33}NHSO_2$— | Cl |
| III'-3 | 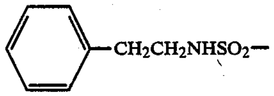 | H |
| III'-4 | 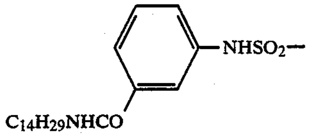 | H |
| III'-5 | $C_{18}H_{37}NHCO$— | H |
| III'-6 | 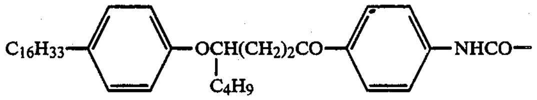 | 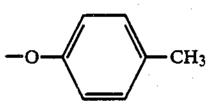 |
| III'-7 | 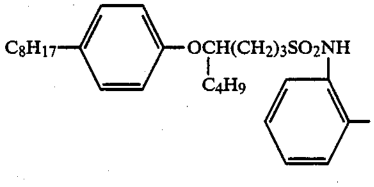 | H |
| III'-8 | 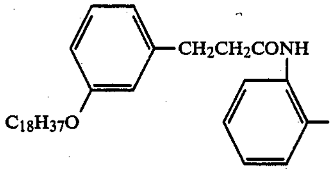 | Cl |
| III'-9 | $C_{18}H_{37}NHSO_2CH_2$— | Cl |
| III'-10 | 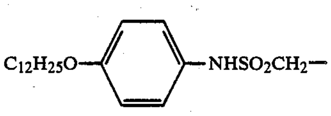 | Cl |
| III'-11 | 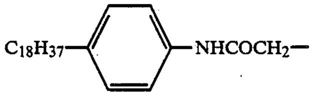 | Cl |
| III'-12 | 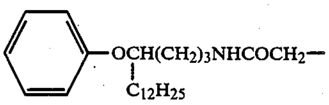 | Cl |

-continued
Formula [III']
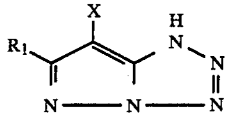
| Compound No. | $R_1$ | X |
|---|---|---|
| III'-13 | 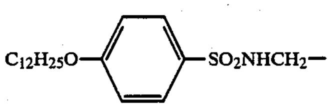 | 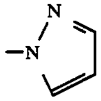 |
| III'-14 | 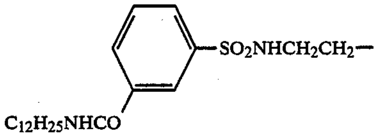 | Cl |
| III'-15 | 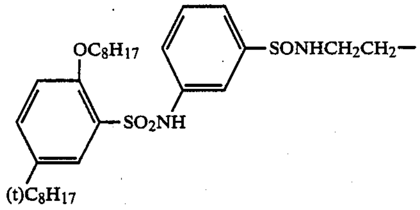 | Cl |
| III'-16 | $C_{16}H_{33}CONHCH_2CH_2—$ | Cl |
Formula [IV']
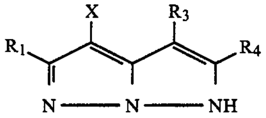
| Compound No. | $R_1$ | $R_3$ | $R_4$ | X |
|---|---|---|---|---|
| IV'-1 | $C_2H_5NHSO_2—$ | H | 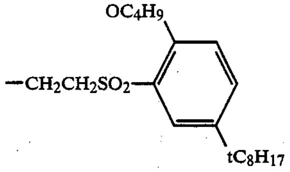 | H |
| IV'-2 | 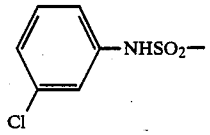 | H | 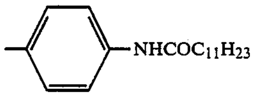 | H |
| IV'-3 | $CH_3NHSO_2—$ | $—CH_3$ | 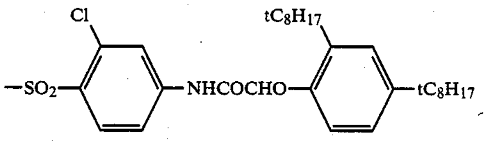 | 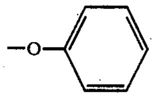 |
| IV'-4 | $CH_3NHCO—$ | H | 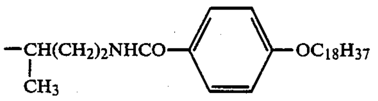 | Cl |

-continued
Formula [IV']
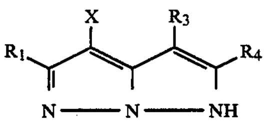
| Compound No. | $R_1$ | $R_3$ | $R_4$ | X |
|---|---|---|---|---|
| IV'-5 | $CH_3NHCO-$ | H | 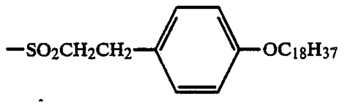 | Cl |
| IV'-6 | 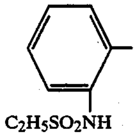 | $-CH_3$ | 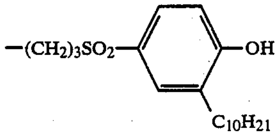 | Cl |
| IV'-7 | 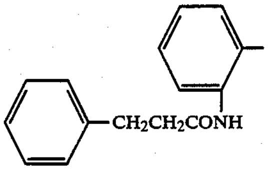 | H | 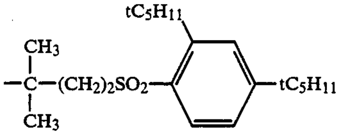 | Cl |
| IV'-8 | 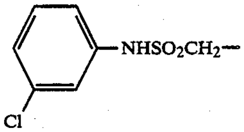 | $-CH_3$ | $-SO_2NH(C_{12}H_{25})$ | H |
| IV'-9 | $CH_3NHCOCH_2-$ | H | 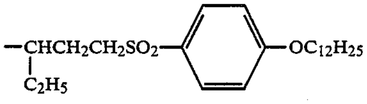 | Cl |
| IV'-10 | 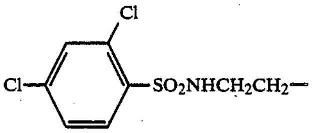 | H | $-OSO_2C_{18}H_{37}$ | Cl |
Formula [V']
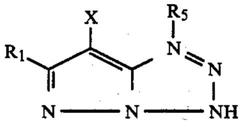
| Compound No. | $R_1$ | $R_5$ | X |
|---|---|---|---|
| V'-1 | $C_{18}H_{37}NHSO_2-$ | H | H |
| V'-2 | 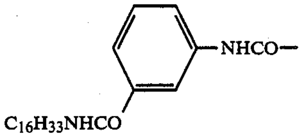 | $-CH_3$ | Cl |
-continued
Formula [V']
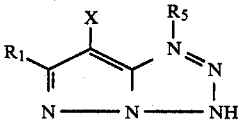
| Compound No. | $R_1$ | $R_5$ | X |
|---|---|---|---|
| V'-3 | 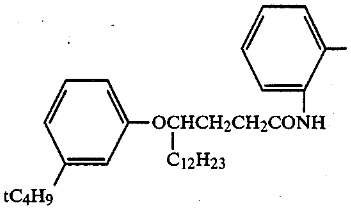 | H | Cl |

-continued

Formula [V']

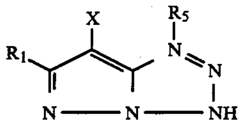

| Compound No. | $R_1$ | $R_5$ | X |
|---|---|---|---|
| V'-4 | $C_{12}H_{25}NHSO_2CH_2$— | H | Cl |

The cyan couplers of the invention may readily be prepared with reference to J. Chem. Soc., Perkin I, 2047, (1977), J. Heterocycl. Chem., ii, 423 (1974), Ber. 32, 797 (1899), Chem. Ber., 95, 2861, 2881 (1962), U.S. Pat. Nos. 3,705,896 and 3,725,067, Japanese Patent Examined Publication No. 43947-1971, Japanese Patent O.P.I. Publication Nos. 220346-1985 and 43659-1985, Japanese patent application No. 120054-1986 and so forth.

Typical synthesis examples will be given below.

SYNTHESIS EXAMPLE 1 (SYNTHESIS OF I'-2)

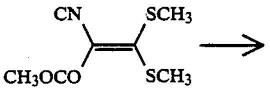

a

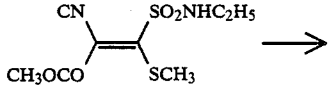

b

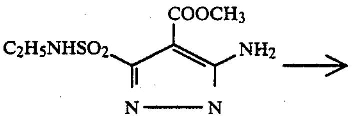

c

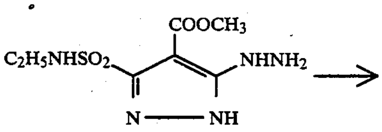

d

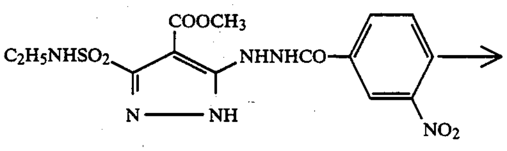

e

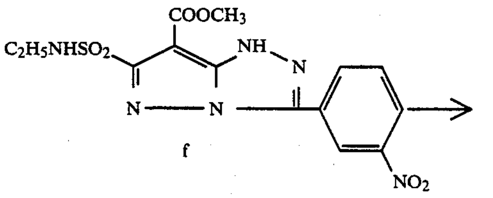

f

-continued

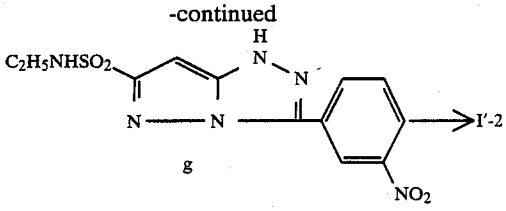

g

SYNTHESIS EXAMPLE 1 (SYNTHESIS OF I'-2)

[a→b]

a of 0.10 moles and 0.22 mols of sodium diethylaminosulfinate were dissolved in 400 ml of methanol and the solution was refluxed .for 35 hours with heating. The solvent was distilled off and the resulted residues was added with acetic acid to filtrate impurities. The resulted filtrates were concentrrated, so that 0.060 mols of b were obtained.

[b→c]

b of 0.060 mols was added with 300 ml of ethanol and 0.070 mols of a 100% hydrazine hydrate were dropped into the resulted solution. After the solution was reflexed for 7 hours with heating, the solvents were distilled off and the residues were recrystallized with ethanol, so that 0.040 mols of c were obtained.

[c→d]

c of 0.040 mols was added with 150 ml of 6N hydrochloric acid. Then, an aqueous solution containing 2.3 g of sodium nitrite was dropped into the resulted solution at 0° C. and stirred for 30 minutes. In addition, a hydrochloric acid solution containing 15 g of stannous chloride dihydrate was dropped thereinto at −5° C. After stirring for 30 minutes, the solution was stirred for 1.5 hours at room temperature and was then added with 400 ml of water. The resulted crystals were filtrated by blowing hydrogen sulfide gas and washed with water and then with ethano, so that 0.030 mols of d were obtained.

[d→e]

A solution was prepared by dissolving 0.030 mols of d in 70 ml of acetonitrile. m-nitrobenzoyl chloride of 0.036 mols and triethylamoine of 0.3 mols were dropped into the solution and stirred for 4 hours at room temperature. The resulted crystals were filtrated, so that 0.026 mols of e were obtained.

[e→f]

e of 0.026 mols and phosphorus oxychloride of 0.030 mols were added to 200 ml of toluene. The solution prepared was refluxed for 4 hours with heating. After the toluene was distilled off. 0.30 mols of pyridine and 150 ml of acetonitrile were added. The resulted matter was further refluxed for 2.5 hours with heating and was then filtrated when it was still warn, so that 0.013 mols of f were obtained.

[f→g]

A solution was prepared by adding 0.013 mols of f to a mixed solvent of 50 ml of acetic acid, 14 ml of sulfuric acid and 1.5 ml of water and was then refluxed for 2 hours with heating. The refluxed matter was neutralized in an aqueous sodium hydroxide solution and was then extracted and condensed with ethyl acetate.

Thereafter, water was added, so that 0.009 mols of a deposition g were obtained.

[g→I'-2]

A solution was prepared by dissolving 0.009 mols of g into 100 ml of THF and was then hydrogenated with Pd/C. After the Pd/C was filtrated, the solvents were distilled off. The resulted residues were dissolved in 150 ml of acetonitrile and, thereto 0.010 mols of octadecanecarbonyl chloride were added and 0.012 mols of pyridine were then dropped. After stirred for 2.5 hours at room temperature, the deposited crystals were filtrated and were then recrystallized with ethyl acetate, so that 0.0072 mols of white needle shaped crystals, I'-2, were obtained.

SYNTHESIS EXAMPLE 2 (SYNTHESIS OF I'-33)

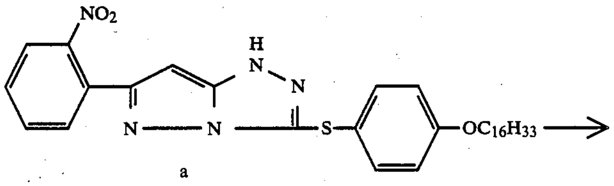

a

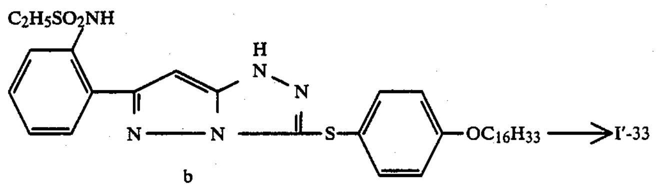

b

[Synthesis of a]

In 250 ml of amyl alcohol, 0.12 mols of ethyl-o-nitrobenzoyl acetate and 0.10 mols of S-(p-hexadecaneoxy)-phenylisothiocarbohydrazine hydroiodide were refluxed for one hour with heating. When this reaction solution was cooled down, yellow crystals were deposited. The cyrstalls were filtrated and were then recrystallized with scetonitrile, so that 0.023 mols of a were obtained.

[a→b]

A hydrogenation reduction of 0.023 mols of a were carried out with Pd/C in the same manner as in the [g→I'-2] processof Synthesis Example 1. Then, 0.018 mols of b were obtained by reacting with ethylsulfonyl chloride.

[b→I'-33]

A solution was prepared by dissolving 0.018 mols of b in 30 ml of acetic acid. Then, 6 ml of an aqueous 35% hydrogen peroxide were gradually dropped thereinto. After stirred for 2 hours at 55° C., 100 ml of water were added. The resulted solution was neutralized gradually with an aqueous sodium hydroxide solution to adjust the pH to be within the range of from pH 6.5 to 7.0. The resulted reaction solution was extracted with ethyl acetate and the solvents were then distilled off. The obtained deposition was washed with cooled acetonitrile, so that 0.014 mols of light-yellow needle shaped crystals, I'-33, were obtained.

SYNTHESIS EXAMPLE 3 (SYNTHESIS OF II'-2)

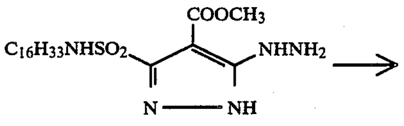

a

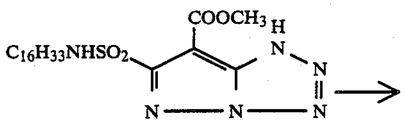

b

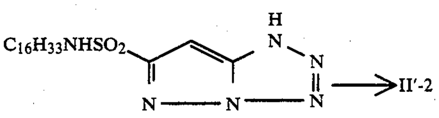

c a was synthesized in the same manner as in the synthesis process for d in Synthesis Example 1.

[a→b]

A solution was prepared by dissolving 0.10 mols of a into 70 ml of 6N hydrochloric acid and was then dropped with 100 ml of an aqueous solution containing 0.107 mols of sodium nitrite at 0° C. After stirred for 1.5 hours, the solution was neutralized gradually with an aqueous sodium hydroxide solution. The resulted reaction solution was extracted with ethyl acetate and the solvents were distilled off. The resulted residues were then recrystallized with acetonitrile, so that 0.040 mols of b were obtained.

[b→c]

A solution was prepared by adding 0.040 mols of b into a mixed solvent of 160 ml of acetic acid, 46 ml of sulfuric acid and 4.9 ml of water and was then refluxed for 2 hours with heating. The refluxed matter was neutralized with an aqueous sodium hdyroxide solution and was then extracted with ethyl acetate. After the extracted matter was condensed, the condensed matter was poured into 100 ml of water, so that a deposition of c (in an amount of 0.021 mols) was filtrated.

[c→II'-2]

A solution was prepared by dissolving 0.021 mols of c in 350 ml of chloroform and was then added with 0.034 mols of N-chlorosuccinimide. After stirred for 30 minutes at room temperature, the solvents were distilled off and the resulted matter was recrystallized with ethyl acetate, so that 0.014 mols of white powered crystals, II'-2, were obtained.

The cyan couplers relating to the invention each represented by the above-given Formula [VI] are the compounds of pyrazolobenzimidazole type containing at least one hydrogen-bondable group. The hydrogen-bondable group has an active hydrogen atom which is capable of forming a hydrogen bond with a nitrogen atom in the pyrazolobenzimidazole ring.

The typical examples of the preferable hydrogen-bondable groups include the following.

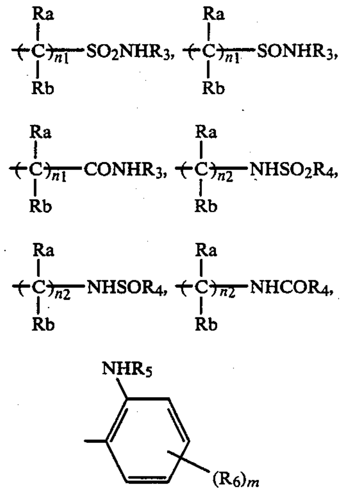

wherein Ra, Rb, $R_3$, $R_4$ and $R_5$ independently represent a hydrogen atom or a substituent, $R_6$ represents a substitutent, $n_1$ is an integer of zero or 1, $n_2$ is 1 or 2 and m is an integer of 0 through 4, provided that when m is 2 or more, respective $R_6$'s may be the same with or the different from each other.

Ra, Rb and $R_4$ independently represent a hydrogan atom, an alkyl group, an aryl group, a heterocyclic residual group and so forth;

$R_3$ represents, preferably, a hdyrogen atom, an alkyl group, an aryl group, a heterocyclic residual group and, besides, a sulfonyl group, a sulfinyl group, a carbonyl group and so forth each of which may be substituted with an alkyl group, an aryl group or the like.

$R_5$ represents a hydrogen atom, an alkyl group, an aryl group, a heterocyclic residual group and, besides, a sulfonyl group, a sulfinyl group, a carbonyl group and so forth each of which may be substituted with an alkyl group, an aryl group or the like, and the preferable ones represented by $R_5$ include the sulfonyl group, sulfinyl group and carbonyl group;

There is no special limitation to the substituents represented by $R_6$.

The above-given substituents are also allowed to contain a substituent including ballast groups such as a long-chained hydrocarbon group, a polymer residual group, and so forth.

In the invention, the particularly preferably hydrogenbondable groups represented by $R_1$ include the following groups. Namely,

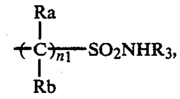

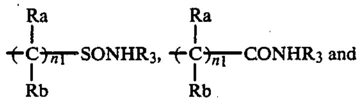

and

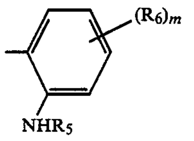

and, among them, the further preferable ones include $—SO_2NHR_3$, $—SONHR_3$, $CONHR_3$ and

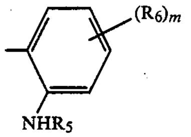

There is no special limitation to the substituents each represented by $R_2$ denoted in Formula [VI].

The typical examples thereof include each group of alkyl, aryl, anilino, acylamino, sulfonamido, alkylthio, arylthio, alkenyl, cycloalkyl and so forth and, besides a halogen atom, each group of cycloalkenyl, alkinyl, heterocyclic, sulfonyl, sulfinyl, phosphonyl, acyl, carbamoyl, sulfamoyl, cyano, sulfonyloxy, alkoxy, aryloxy, hetercyclicoxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl and heterocyclic-thio and, in addition, a spiro compound residual group, a cross-linked hydrocarbon compound residual group and, further, each group of thioureido, carboxy, hydroxyl, mercapto, nitro, sulfonic acid and so forth.

The alkyl groups represented by $R_2$ preferably include those having 1 to 32 carbon atoms. They may also be straight-chained or branched.

The aryl groups represented by $R_2$ preferably include a phenyl group.

The acylamino groups represented by $R_2$ include an alkylcarbonylamino group, an arylcarbonylamino group and so forth.

The sulfonamido groups represented by $R_2$ include an alkylsulfonylamino group, an arylsulfonylamino group and so forth.

The alkylthio groups, and the alkyl and aryl components of the arylthio group each represented by $R_2$ include the alkyl group and aryl group each represented by the above-given R.

The alkenyl groups represented by $R_2$ include those having 2 to 32 carbon atoms, the cycloalkyl groups include those having 3 to 12 carbon atoms and, more preferably, those having 5 to 7 carbon atoms. The alkenyl groups may be straight-chained or branched.

The cycloalkenyl groups represented by $R_2$ include those having 3 to 12 carbon atoms and, more preferably, those having 5 to 7 carbon atoms.

The sulfonyl groups represented by $R_2$ include an alkylsulfonyl group, an arylsulfonyl group and so forth;

The sulfinyl groups include an alkylsulfinyl group, an arylsulfinyl group and so forth;

The phosphonyl groups include an alkylphosphonyl group, an alkoxyphosphonyl group, an aryloxyphosphonyl group, an arylphosphonyl group and so forth;

The acyl groups include an alkylcarbonyl group, an arylcarbonyl group and so forth;

The carbamoyl groups include an alkylcarbamoyl group, an arylcarbamoyl group and so forth;

The sulfamoyl groups include an alkylsulfamoyl group, an arylsulfamoyl group and so forth:

The acyloxy groups include an alkylcarbonyloxy group, an arylcarbonyloxy group and so forth;

The carbamoyloxy groups include an alkylcarbamoyloxy group, an arylcarbamoyloxy group and so forth;

The ureido groups include an alkylureido group, an arylureido group and so forth;

The sulfamoylamino groups include an alkylsulfamoylamino group, an arylsulfamoylamino group and so forth;

The heterocyclic groups include, preferably, those having a 5- to 7-membered ring including, typically, a 2-furyl group, a 2-thienyl group, a 2-pyrimidinyl group, a 2-benzothiazolyl group, a 1-pyrrolyl group, a 1-tetrazolyl group and so forth;

The heterocyclic-oxy groups include, preferably, those having a 5- to 7-membered ring including, for example, a 3,4,5,6-tetrahydropyranyl-2-oxy group, a 1-phenyltetrazole-5-oxy group and so forth;

The heterocyclic-thio groups include, preferably, those having a 5- to 7-membered ring including, for example, a 2-pyridylthio group, a 2-benzothiazolylthio group, a 2,4-diphenoxy-1,3,5-triazole-6-thio group and so forth;

The siloxy groups include, a trimethylsiloxy group, a triethylsiloxy group, a dimethylbutylsiloxy group and so forth;

The imido groups include a succinimido group, a 3-heptadecylsuccinimido group, a phthalimido group, a glutarimido group and so forth;

The spiro compound residual groups include a spiro [3.3] heptane-1-yl and so forth;

The cross-linked hdyrocarbon compound residual groups include bicyclo [2.2.1] heptane-1-yl, tricyclo [3.3.1.1$^{3\,7}$] decane-1-yl, 7,7-dimethyl-bicyclo [2.2.1] heptane-1-yl and so forth;

The carbonylamino groups include each group of alkoxycarbonylamino, aryloxycarbonylamino and so forth;

The above-given groups are also allowed to contain a substituent including ballast groups and the like such as a long-chained hdyrocarbon group, a polymer residual group and so forth.

In the couplers represented by the aforegiven Formula [VI], which relate to this invention, it is particularly preferable that $R_2$ represents an electron withdrawing group. Such electron withdrawing groups should preferably be those having not less than +20 of a substituent constant δp which is defined by Hammett. The typical examples of these substituents include each group of sulfonyl, sulfinyl, sulfonyloxy, phosphoryl, pyrrolyl, tetrazolyl, cyano, acyl, acyloxy, carboxyl, sulfo, oxycarbonyl, nitro, sulfamoyl, carbamoyl and so forth, and a halogen atom. Besides the above, the following substituents may also be useful. Namely, each group of α-halogenated alkyl, α-halogenated alkoxy, tetrafluoroaryl, pentafluoroaryl, tetrafluoroaryloxy, pentafluoroaryloxy, alkylsulfonylmethyl, arylsulfonylmethyl and so forth. Among the above-given substituents, the particularly preferable electron withdrawing groups include each group of sulfonyl, sulfinyl, sulfonyloxy, sulfamoyl, carbamoyl and cyano.

The substituents represented by X, which are capable of splitting off upon reaction with the oxidized product of a color developing agent, include, for example, a halogen atom such as a chlorine atom, a bromine atom, a fluorine atom and so forth and each of the groups including alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring bonded to an N atom, alkyloxycarbonylamino, aryloxycarbonylamino, carboxyl,

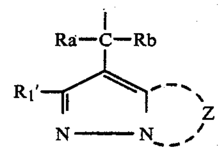

wherein $R_1'$ is synonymous with the aforegiven $R_1$, Ra and Rb each represent a hydrogen atom, an aryl group, an alkyl group or a heterocyclic group; and Z represents a group of non-metal atoms necessary to complete a nitrogen-containing heterocyclic ring; the nitrogen-containing heterocyclic rings are allowed to have a substituent and more preferably include a benzimidazole ring that is a part of the structure completing the couplers represented by Formula [VI]. Among them, a halogen atom is preferable. The particularly preferable ones represented by X are a hydrogen atom and a chlorine atom.

In Formula [VI], Y represents a hydrogen atom or a substituent. The preferable substituents represented by Y include, for example, those capable of releasing from the compound of the invention upon reaction of the compound with the oxidized product of a color developing agent. For example, the substituents represented by Y include a group capable of releasing under an alkaline condition, such as those described in Japanese Patent Publication Open to Public Inspection No. 228444-1986 and so forth, a substituent capable of coupling off upon reaction with the oxidized product of a color developing agent such as those described in Japanese Patent O.P.I. Publication No. 133734-1981, and so forth.

Y is preferably a hydrogen atom.

The compounds represented by Formula [VI] may be more preferably represented by the following Formula [VI'].

Formula [VI']

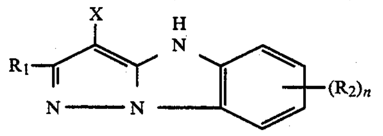

In Formula [VI'], $R_1$, $R_2$, n and X are synonymous with those denoted in Formula [VI].

The typical examples of the compounds of the invention will be given below.

Formula [VI']
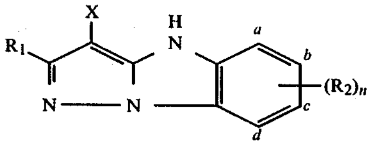
| Compound No. | $R_1$ | Position | $R_2$ | X |
|---|---|---|---|---|
| VI'-1 | $C_{18}H_{37}NHSO_2-$ | | H | Cl |
| VI'-2 | 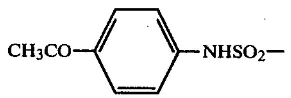 | b | $-C_{11}H_{22}OH$ | H |
| VI'-3 | 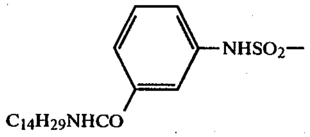 | b | $-SO_3H$ | Cl |
| VI'-4 | $tC_4H_9NHSO_2-$ | b | 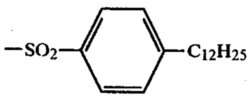 | H |
| VI'-5 | $C_6H_5NHSO_2-$ | c | $-SO_2NHC_{12}H_{25}$ | H |
| VI'-6 | 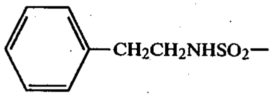 | b<br>d | $-COOC_{12}H_{25}$<br>$-Cl$ | Cl |
| VI'-7 | $CH_3NHSO_2-$ | c | $-SO_2C_{18}H_{37}$ | H |
| VI'-8 | $C_{16}H_{33}NHSO_2-$ | c | $-COCH_3$ | $-SO_3H$ |
| VI'-9 | 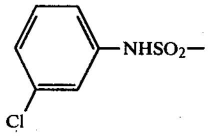 | b | $-CONHC_{12}H_{25}$ | H |

-continued
Formula [VI']
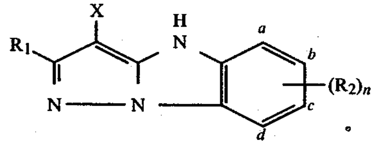
| Compound No. | $R_1$ | Position | $R_2$ | X |
|---|---|---|---|---|
| VI'-10 | 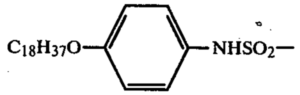 | b | $-CF_3$ | H |
| VI'-11 | 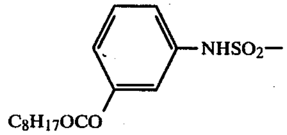 | c | $-COOH$ | 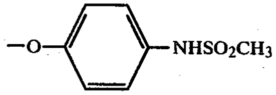 |
| VI'-12 | $C_8H_{17}NHSO-$ | | H | H |
| VI'-13 | 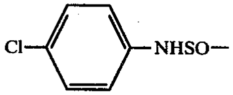 | c | $-OSO_2C_8H_{17}$ | H |
| VI'-14 | $C_2H_5NHCO-$ | c | $-NHCOC_{12}H_{25}$ | Cl |
| VI'-15 | 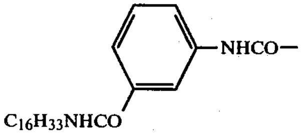 | c | $-COOH$ | H |
| VI'-16 | $tC_4H_9NHCO-$ | b | 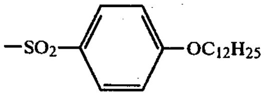 | H |
| VI'-17 | 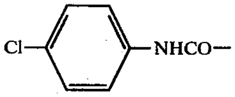 | b | 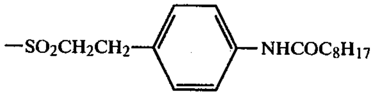 | H |

-continued
Formula [VI']
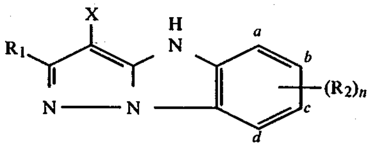
| Compound No. | $R_1$ | Position | $R_2$ | X |
| --- | --- | --- | --- | --- |
| VI'-18 | $C_8H_{17}NHCO-$ | c | $-CONHC_8H_{17}$ | H |
| VI'-19 | 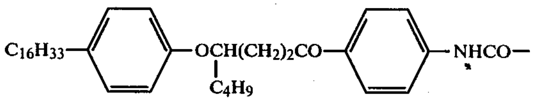 | b<br>c | $-Cl$<br>$-Cl$ | 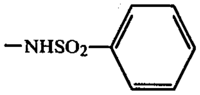 |
| VI'-20 | $C_3H_7NHCO-$ | c | $-SO_2NHC_{11}H_{25}$ | Cl |
| VI'-21 | 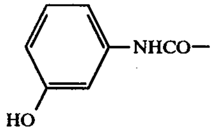 | b | $-COOC_{12}H_{25}$ | H |
| VI'-22 | 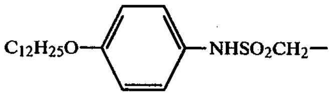 | b | $-OCH_3$ | Cl |
| VI'-23 | $C_2H_5NHSO_2CH_2-$ | c | $-CONHC_{12}H_{25}$ | 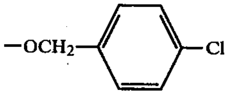 |
| VI'-24 | 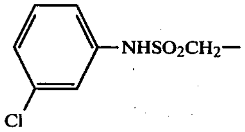 | b | 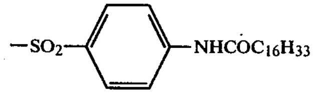 | H |
| VI'-25 | $C_{11}H_{23}NHSO_2CH_2-$ | c | $-CN$ | H |
| VI'-26 | $C_{18}H_{37}NHSO_2CH_2-$ | c | $-COCH_3$ | H |
| VI'-27 | $C_6H_5NHSO_2CH_2-$ | b | $-SO_2N(C_8H_{17})_2$ | Br |
| VI'-28 | $C_2H_5NHSOCH_2-$ | b | $-OCOC_{11}H_{23}$ | H |

-continued
Formula [VI']
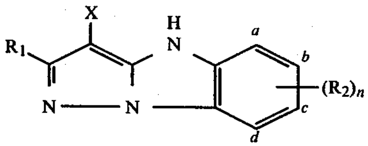
| Compound No. | $R_1$ | Position | $R_2$ | X |
|---|---|---|---|---|
| VI'-29 | $C_{11}H_{23}NHCOCH_2$— | | H | 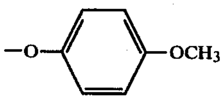 |
| VI'-30 | 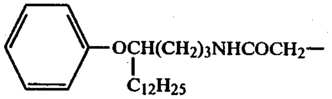 | c | —F | H |
| VI'-31 | 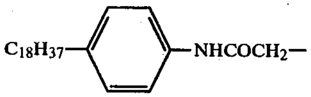 | b | 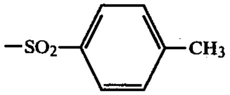 | H |
| VI'-32 | 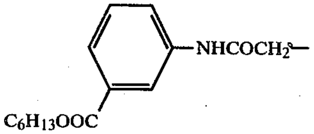 | b | $—CF_3$ | H |
| VI'-33 | $C_2H_5NHCOCH_2$— | c | $—SO_2NHC_8H_{17}$ | Cl |
| VI'-34 | $C_8H_{17}SO_2NHCH_2$— | b<br>d | —Cl<br>—Cl | Cl |
| VI'-35 | 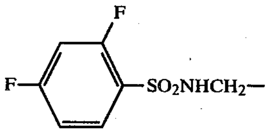 | c | $—CONHC_{10}H_{21}$ | H |
| VI'-36 | $C_7H_{15}CONHCH_2$— | b | $—SO_3H$ | Cl |
| VI'-37 | 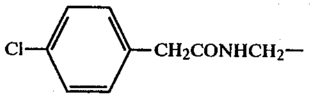 | c | $—OC_8H_{17}$ | 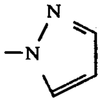 |

-continued
Formula [VI']
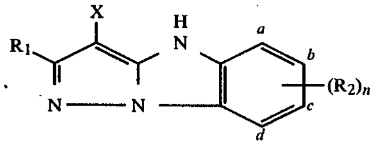
| Compound No. | $R_1$ | Position | $R_2$ | X |
|---|---|---|---|---|
| VI'-38 | $-C_6H_5SO_2NHCH_2CH_2-$ | b | $-tC_8H_{17}$ | Cl |
| VI'-39 | 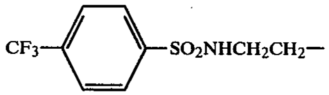 | c | 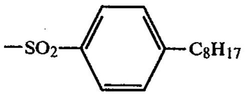 | H |
| VI'-40 | 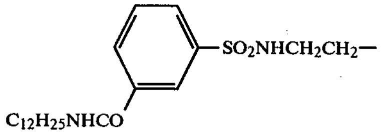 | b | $-CN$ | H |
| VI'-41 | $C_4H_9SONHCH_2CH_2-$ | b | $-COOC_{12}H_{25}$ | H |
| VI'-42 | 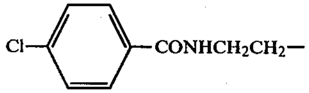 | b | 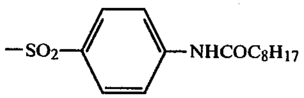 | $-SO_3H$ |
| VI'-43 | $C_3H_7CONHCH_2CH_2-$ | b | $-COOC_{12}H_{25}$ | Cl |
| VI'-44 | 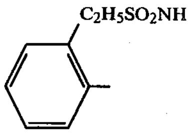 | d<br>c | $-Cl$<br>$-OC_{11}H_{23}$ | H |
| VI'-45 | 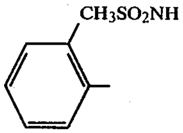 | c | 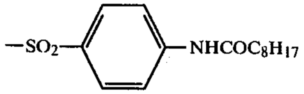 | H |

-continued
Formula [VI']
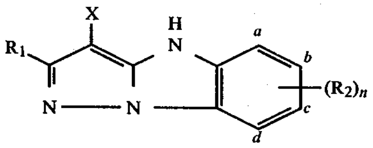
| Compound No. | R1 | Position | R2 | X |
|---|---|---|---|---|
| VI'-46 | 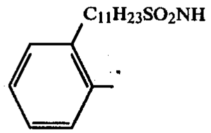 | b<br>c | —Cl<br>—Cl | Cl |
| VI'-47 | 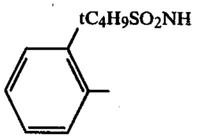 | c | $-CONHC_{11}H_{23}$ | H |
| VI'-48 | 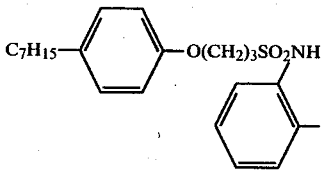 | c | $-SO_2NHC_2H_5$ | 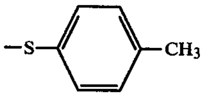 |
| VI'-49 | 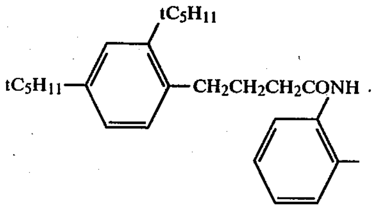 | | H | Cl |
| VI'-50 | 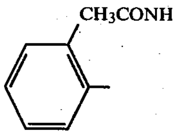 | c | $-SO_2C_{16}H_{33}$ | H |

-continued
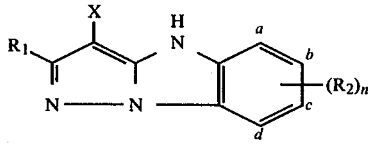
Formula [VI']
| Compound No. | $R_1$ | Position | $R_2$ | X |
|---|---|---|---|---|
| VI'-51 | 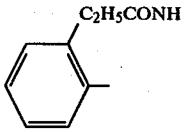 | c | $-CON(C_8H_{17})_2$ | H |
| VI'-52 | 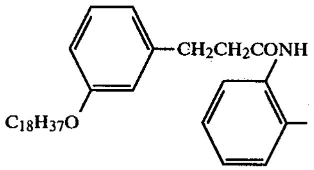 | c | $-COCH_3$ | Cl |

These cyan couplers of the invention may readily be synthesized with reference to U.S. Pat. Nos. 3,061,432, 3,212,894 and 3,369,897, British Pat. Nos. 1,047,612, 918,128 and 585,780, German Pat. No. 1,070,030, Japanese Patent Examined Publication Nos. 10068-1971, 10479-1971 and 24080-1974, Japanese Patent O.P.I. Publication No. 26541-1976 and so forth.

The typical synthesis examples of the compounds of the invention will be given below.

SYNTHESIS EXAMPLE 1 (SYNTHESIS OF COMPOUND 18)

[b→c]

b of 0.047 mols were suspended in 250 ml of methanol and the suspension was adjusted to be pH 8 with an aqueous sodium hydroxide solution. The resulted solution was hydrogenated for 2 hours at 50 air pressure under the presence of Raney nickel and was then heated for 10 minutes at 60° C. The filtrate from which the catalysts had been separated was refined with active carbon. When it was cooled to be acidified with hydrochloric acid, c was deposited. The resulted c was filtrated, washed with water and then with cooled ace-

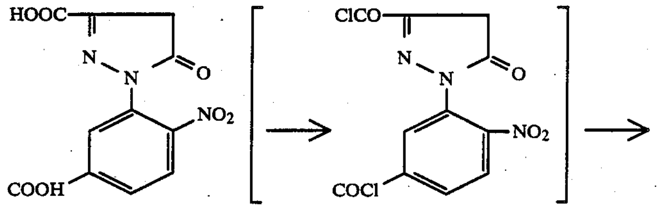

a

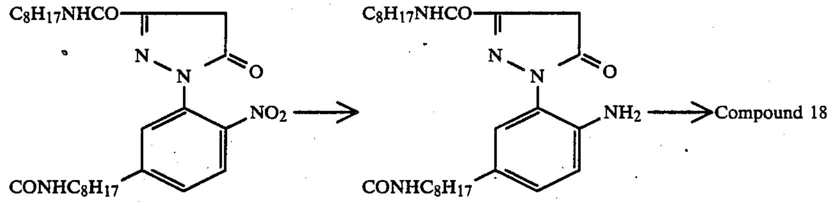

b c

SYNTHESIS EXAMPLE 1

[Synthesis of a]

A solution of 0.2 mols of 4-nitro -3-amino-benzoic acid was made in 100 ml of 5N dilute hydrochloric acid. While the solution was cooled down to 0° C., 100 ml of an aqueous solution containing 0.2 mols of sodium nitrite were added. After stirred for one hour, the resulted solution was gradually added into an aqueous 2.5N sodium hydroxide solution containing 0.2 mols of ethylcyan succinate.

After stirred for another one hour, the solution was heated up to 90° C. taking 30 minutes and was then neutralized. The resulted deposition was filtered and recrystallized with ethyl acetate, so that 0.11 mols of a were obtained.

[a→b]

A solution of 100 ml of dichloromethane containing 25 ml of thionyl chloride was dropped into 200 ml of a dichloromethane solution containing 0.11 mols of a and 30 ml of triethylamine and the resulted solution was stirred for one hour. After ice water was added and stirred, an organic layer was separated and the solvents were distilled off. The resulted residues were dissloved in 200 ml of acetonitrile and thereto 30 ml of pyridine and 0.25 mols of octylamine were added. The resulted solution was stirred for 1.5 hours and was then further stirred for 3 hours at 55° C. Thereafter, 600 ml of water were poured thereinto. The resulted depositions were filtrated and were then recrystallized with ethyl acetate, so that 0.047 mols of b were obtained.

tone, so that 0.034 mols of c were obtained.

[c→Compound 18]

c of 0.034 mols were dissolved in 160 ml of n-propanol. The resulted solution was adjusted to be pH 4 with hydrochloric acid and was refluxed for 5 hours with heating. After then, it was cooled down and neutralized with an aqueous sodium hydroxide solution. Thereto, 400 ml of water were added and stirred. After the resulted precipitates were filtrated and washed with water, they were recrystallized with acetonitrile, so that 0.019 mols of white needle shaped crystals, Compound 18, were obtained.

SYNTHESIS EXAMPLE 2 (SYNTHESIS OF COMPOUND 46)

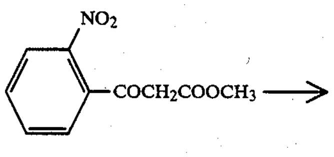

a

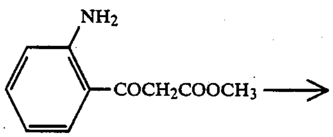

b

-continued

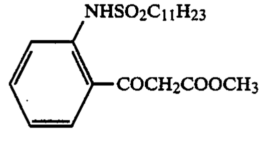

b

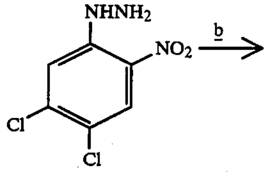

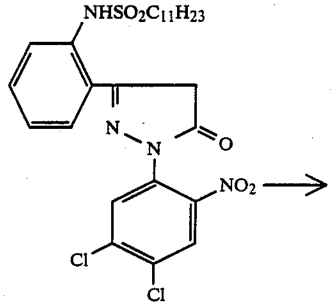

c

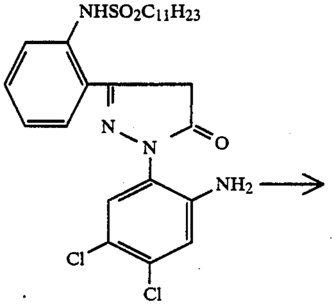

d

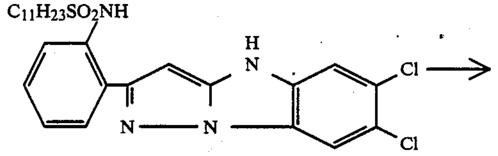

e

Compound 46

SYNTHESIS EXAMPLE 2

[a→b]

a of 0.30 mols was dissolved in 500 ml of THF and was then hydrogenated with Pd/C. After the Pd/C was filtrated, the solvents were distilled off. The resulted residues were dissolved in 600 ml of acetonitrile. To the resulted solution, 0.32 mols of undecanesulfonyl chloride were added at room temperature and 0.34 mols of pyridine were dropped. After the solution was stirrred for 2.5 hours at room temperature, the resulted reaction solution was condensed by one half. To the concentrate, 500 ml of water were poured and the deposited crystals were filtrated and were then recrystallized with ethyl acetate, so that 0.21 mols of b were obtained.

[Synthesis of c]

To an aqueous solution of 240 ml containing 6.8 g of saodium hydroxide, 0.17 mols of 2-nitro-4,5-dichlorophenyl hydrozine were added. After the solution was dissolved with heating, it was cooled down and neutralized with 1N hydrochloric acid. The resulted solution was added with 0.21 mols of b and was then stirred for 7 hours with heating at 110° C. After it was allowed to cool, the deposited solid matters were filtrated and were then recrystallized with ethyl acetate, so that 0.098 mols of c were obtained.

[c→d→e]

A hydrogenation was carried out in the same manner as in the process of [b→c] of Synthesis Example 1, so that 0.074 mols of d were obtained. Further, a closed-ring reaction was carried out in the same manner as in the process of [c→ Compound 18], so that 0.040 mols of e were obtained.

[e→Compound 46]

To 400 ml of glacial acetic acid containing 4 g of sodium acetate, 0.040 mols of e were dissolved. Under the nitrogen-atmosphere at 40° C., 0.06 mols of sulfuryl chloride were gradually added and the resulted solution was stirred for one hour at room temperature.

The resulted products were filtrated and washed with water, they were recrystallized with methanol, so that 0.027 mols of white powered crystals, Compound 46, were obtained.

The cyan couplers of the invention may be used in an amount of, normally, from $1\times10^{-3}$ mol to 1 mol and, preferably, from $1\times10^{-2}$ mol to $8\times10^{-1}$ mol.

The couplers of the invention may also be used together with other kinds of cyan couplers in combination.

In the present invention, cyan dye image-forming couplers represented by formulas [VII] and [VIII] are also advantages and they may be used either singly or in combination with those represented by formulas [I] through [VI]

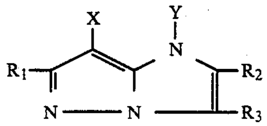

[VII]

wherein $R_1$ and $R_2$ each represent a hydrogen atom, a substituent or a group having an active hydrogen atom capable of forming a hydrogen bond provided that at least one of $R_1$ and $R_2$ is a group having an active hydrogen atom capable of forming a hydrogen bond, Y and $R_3$ independently represent a hydrogen atom or a substituent as defined for the compound represented by formula [I], and X is a hydrogen atom or a substituent capable of being split off upon reaction with the oxydized product of a color developing agent as defined for the compound of formula [I];

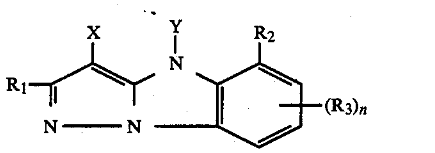

[VIII]

wherein $R_2$ represents a group having an active hydrogen atom capable of forming a hydrogen bond as defined for the compound of formula [VI], $R_3$ is an hydrogen atom or a substituent as defined in formula [VI], n is an integer of 0 to 3 provided that when n is 2 or more $R_3$'s may be the same with or different from each other, $R_1$ and Y independently represent a hydrogen atom or a substituent as defined in formula [I] and X is a hydrogen atom or a substituent capable of being split off upon reaction with the oxydized product of a color developing agent as defined for the compound of formula [I].

The cyan couplers of the invention may similarly be applied with any processes and techniques which may also be applied to ordinary types of cyan dye forming couplers. Typically, a color light-sensitive material of the invention $R_1$ and $R_2$ represent a hydrogen atom, a substituent or a group having an active hydrogen atom capable of forming a hydrogen bond provided that at least one of $R_1$ and $R_2$ is a group having an active hydrogen atom capable of forming a hydrogen bond may be prepared in such a manner that the cyan couplers of the invention are compounded into a silver halide emulsion so that the emulsion is coated over to a support.

The color photographic light-sensitive materials of the invention may take such a form as a color negative or positive film, a color print paper and so forth.

The light-sensitive materials of the invention including the above-given color print paper may be for monochromatic and multicolor use, either. In the multicolor light-sensitive materials, the cyan couplers of the invention may be contained in any layers. It is however preferable to contain them into a red light-sensitive silver halide emulsion layer.

The above-mentioned multicolor light-sensitive materials each have dye image forming component units which are sensitive to the three primary color regions of spectra, respectively. Each of the component units may be comprised of a single-coated or mutlicoated emulsion layer sensitive to a certain spectral region. The component layers of a light-sensitive material, icncluding the image forming component units layer, may be arranged in various order as known in the art. A typical multicolor light-sensitive material is comprised of a support bearing thereon, respectively, a cyan dye image forming component unit comprising at least one red light-sensitive silver halide emulsion layer containing at least one of cyan couplers of which at least one cyan coupler is of the invention; a magenta dye image forming component unit comprising at least one green light-sensitive silver halide emulsion layer containing at least one of magenta couplers of which at least one magenta coupler; and a yellow dye image forming component unit comprising at least one blue light-sensitive silver halide emulsion layer containing at least one of yellow couplers of which at least one yellow coupler.

Such light-sensitive materials are also allowed to have such an additional layer as a filter layer, an interlayer, aprotective layer, a subbing layer and so forth.

The cyan couplers of the invention may be contained in an emulsion layer by following any methods having been publicly known so far. A silver halide emulsion applicable to the invention may be prepared in the following process, for example. The cyan couplers of the invention are dissolved independently or in combination in a high boiling organic solvent having a boiling point of not lower than 175° C., such as tricresyl phosphate, dibutyl phthalate and so forth, or in a low boiling solvent such as butyl acetate, butyl propionate and so forth, independently or, if required, in the mixture thereof. The dissolved solution was mixed with an aqueous gelatin solution containing a surface active agent and was then emulsified with a high-speed rotary mixer or a colloid mill. The resulted emulsion is then added to a silver halide.

The silver halide components preferably used in the invention include, for example, silver chloride, silver chlorobromide and silver chloroiodobromide. They may also include a mixture thereof, such as a mixture of silver chloride and silver bromide. To be more concrete, in the case of using a silver halide emulsion in a color print paper, it is preferable to include chlorine atoms as the halide component of silver halides and it is particularly preferable that silver chloride, silver chlorobromide or silver chloroiodobromide each has a silver chloride content of at least 1%, because a particularly rapid developability is required.

Silver halide emulsion layers may be chemically sensitized in an ordinary method and may also be optically sensitized to a desired wavelength region.

With the purposes of preventing fog and/or stabilizing photographic characteristics in the course of manufacturing, storing or photographically processing a light-sensitive material, silver halide emulsions are allowed to contain the compounds which are known as an antofoggant or stabilizer in the photographic industry.

The color light-sensitive materials of the invention are further allowed to contain a color fog inhibitor, a dye image stabillizer, a UV absorbent, an antistatic agent, a matting agent, a surface active agent and so forth, which are usually used in light-sensitive materials.

For the details of the above-given additives, the reference may be made to Research Disclosure, Vol. 176, pp. 22–31, Dec., 1978, for example.

With the color photofraphic light-sensitive materials of the invention, an image may be formed by carrying out the color developing processes which have been publicly known so far in the art.

The color photographic light-sensitive materials relating to the invention may be processes in an alkaline activation bath, provided that the hydrophilic colloidal layers thereof contain a color developing agent which serves as itself or the precursor thereof.

After the color photographic light-sensitive materials of the invention is color developed, they are treated in a bleaching step and a fixing step. The bleaching and fixing treatments may be carried out at the same time.

After the fixing treatment is completed, a washing treatment is usually carried out. It is also allowed to carry out a stabilizing treatment in place of the washing treatment or to carry out the both treatments in combination.

EXAMPLES

This invention will now be described in detail with reference to the following examples. It is, however, to be understood that this invention shall not be limited thereto.

EXAMPLE 1

Sample 1 of a red light-sensitive color light-sensitive material was prepared in such a manner that each of the following layers is coated in order from the side of a paper support polyethylene laminated on both sides thereof. The amount of each compound added will be indicated in terms of one square meter unless otherwise expressly stated. An amount of silver halides will be indicated in terms of an amount of the silver content thereof.

LAYER 1: AN EMULSION LAYER

A red-sensitive emulsion layer comprising 1.2 g of gelatin, 0.30 g of red-sensitive silver chlorobromide emulsion having a silver chloride content of 96 mol%, and 045 g of Comparative Cyan Coupler a which was dissolved in 0.20 g of dioctyl phthalate.

LAYER 2: A PROTECTIVE LAYER

A protective layer containing 0.50 g of gelatin. Also, as a hardener, 2,4-dichloro-6-hydroxy-s-trazine sodium salt was added in an amount of 0.017 g per g of the gelatin used.

Next, Samples 2 through 37 were prepares in exactly the same manner as in Sample 1, except that Comparative Coupler a was replaced by the couplers of the invention shown in Table-1, respectively. (The amount added was in the same mols as that of Sample 1)

Samples 1 through 37 thus prepared were exposed to light through a wedge and were then processed in the following steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-($\beta$-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |

-continued

| | |
|---|---|
| Water to be added to make | 1 liter |
| pH to be adjusted to | pH 10.20 |
| (Bleach-fixer) | |
| Ferric ammonium ethylenediamine-tetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to each of the samples thus processed, the measurements were made respectively each of the maximum spectral absorption wavelengths (λmax), the reflection densities of 420 nm (Dλ420) when the reflection densities of λmax were 1.0, and the half band widths of spectral absorptions (i.e., the difference between a wavelength at a reflection density of 0.5 on the wavelength side longer than λmax and a wavelength at a reflection density of 0.5 on the wavelength side shorter than λmax).

The smaller a value of Dλ420 is, the less an irregular absorption in blue region is. The smaller a value of half band width is, the sharper an absorption is. These facts mean that a color reproducibility is excellent.

FIG. 1 illustrates the absorption spectra of Samples 1, 5 and 17.

Figure 2:
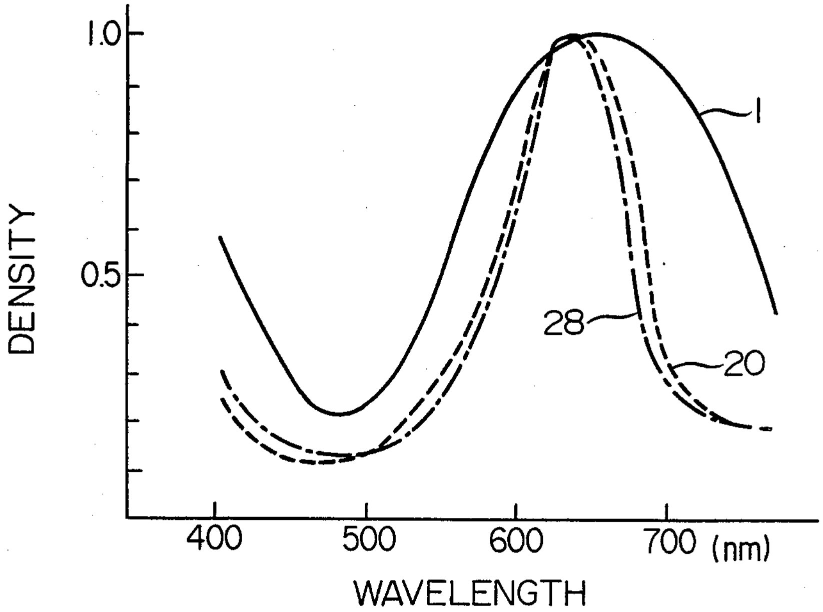
FIG. 2 illustrates the absorption spectra of Samples 1, 20 and 28.

FIG. 2 illustrates the absorption spectra of Samples 1, 20 and 28.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 1-1, wherein the heat and moisture resisting properties of the dye-images are indicated by the precentage of the residual dyes which still remained after the heat and moisture resistance tests were tried, to the initial density of 1.0.

For those measurements, a densitometer, Model KD-7 (manufactured by Konishiroku Photo Ind. Co., Ltd.), was used.

The results will collectively be shown in Table-1.

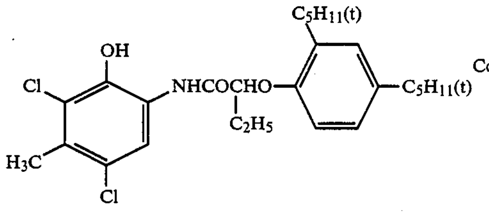

Comparative Coupler a

TABLE 1

| Sample No. | Coupler used | λmax (nm) | W1/2 | Dλ420 | Residual dye (%) |
|---|---|---|---|---|---|
| 1 | Comparative a | 651 | 206 | 0.47 | 60 |

TABLE 1-continued

| Sample No. | Coupler used | λmax (nm) | W1/2 | Dλ420 | Residual dye (%) |
|---|---|---|---|---|---|
| 2 | Compound of This Invention No. I'-1 | 613 | 110 | 0.16 | 100 |
| 3 | Compound of This Invention No. I'-2 | 637 | 106 | 0.29 | 98 |
| 4 | Compound of This Invention No. I'-3 | 624 | 108 | 0.22 | 98 |
| 5 | Compound of This Invention No. I'-4 | 639 | 105 | 0.29 | 99 |
| 6 | Compound of This Invention No. I'-6 | 636 | 111 | 0.27 | 100 |
| 7 | Compound of This Invention No. I'-7 | 634 | 103 | 0.26 | 100 |
| 8 | Compound of This Invention No. I'-16 | 639 | 101 | 0.24 | 97 |
| 9 | Compound of This Invention No. I'-20 | 625 | 103 | 0.21 | 100 |
| 10 | Compound of This Invention No. I'-21 | 622 | 110 | 0.22 | 98 |
| 11 | Compound of This Invention No. I'-26 | 615 | 105 | 0.21 | 98 |
| 12 | Compound of This Invention No. I'-36 | 610 | 112 | 0.19 | 100 |
| 13 | Compound of This Invention No. I'-57 | 608 | 99 | 0.16 | 99 |
| 14 | Compound of This Invention No. I'-60 | 625 | 109 | 0.22 | 98 |
| 15 | Compound of This Invention No. I'-61 | 630 | 110 | 0.26 | 100 |
| 16 | Compound of This Invention No. I'-68 | 624 | 102 | 0.21 | 100 |
| 17 | Compound of This Invention No. I'-72 | 630 | 101 | 0.25 | 99 |
| 18 | Compound of This Invention No. I'-77 | 634 | 108 | 0.26 | 100 |
| 19 | Compound of This Invention No. II'-1 | 613 | 103 | 0.17 | 100 |
| 20 | Compound of This Invention No. II'-3 | 637 | 98 | 0.29 | 98 |
| 21 | Compound of This Invention No. II'-4 | 621 | 101 | 0.21 | 99 |
| 22 | Compound of This Invention No. II'-14 | 610 | 105 | 0.18 | 98 |
| 23 | Compound of This Invention No. II'-19 | 608 | 107 | 0.16 | 100 |
| 24 | Compound of This Invention No. II'-28 | 609 | 109 | 0.17 | 98 |
| 25 | Compound of This Invention No. II'-30 | 611 | 111 | 0.18 | 99 |
| 26 | Compound of This Invention No. II'-32 | 625 | 99 | 0.23 | 100 |
| 27 | Compound of This Invention No. II'-36 | 621 | 102 | 0.20 | 98 |
| 28 | Compound of This Invention No. III'-3 | 633 | 90 | 0.21 | 99 |
| 29 | Compound of This Invention No. III'-4 | 635 | 89 | 0.22 | 100 |
| 30 | Compound of This Invention No. III'-5 | 621 | 98 | 0.18 | 98 |
| 31 | Compound of This Invention No. III'-7 | 620 | 92 | 0.18 | 100 |
| 32 | Compound of This Invention No. III'-9 | 616 | 96 | 0.15 | 98 |
| 33 | Compound of This Invention No. III'-11 | 613 | 91 | 0.15 | 99 |
| 34 | Compound of This Invention No. III'-14 | 609 | 100 | 0.13 | 99 |
| 35 | Compound of This Invention No. III'-16 | 608 | 102 | 0.13 | 100 |
| 36 | Compound of This Invention No. IV'-2 | 605 | 135 | 0.40 | 92 |
| 37 | Compound of This Invention No. IV'-5 | 600 | 138 | 0.37 | 95 |

As is obvious from Table 1, it is found that every sample havng couplers of the invention has excellent spectral absorption characteristics, because the half band widths are extremely narrower and the irregular absorptions represented by Dλ420 are relatively less than those of the samples having the comparative coupler.

It is further found that every sample having the couplers of the invention may be able to provide cyan images which are high in solidity, because of the high percentage of residual dyes resulted from the heat and moisture resistance tests.

In addition, FIGS. 1 and 2 each prove that the couplers of the invention, i.e., Sample Nos. 5, 17, 20 and 28, are relatively less in undesirable irregular absorption caused in green region and relatively sharp in absorption in the regions around λmax, as compared with the conventional phenol type coupler, i.e., Sample 1.

EXAMPLE 2

Samples 38 through 53 were prepared in the same manner as in Example 1, except that 0.20 g of dioctyl phthalate used in Layer 1 of Example 1 were replaced by 1.50 g of trioctyl phthalate.

These samples were exposed and processsed in the same manners as in Example 1. The absorption characteristics and heat and moisture resistance of the images thus obtained were measured.

The results thereof will be shown in Table-2, below.

TABLE 2

| Sample No. | Coupler used | λmax (nm) | W1/2 | Dλ420 | Residual dye (%) |
|---|---|---|---|---|---|
| 38 | Comparative a | 651 | 200 | 0.47 | 60 |
| 39 | Compound of This Invention No. VI'-1 | 630 | 125 | 0.29 | 100 |
| 40 | Compound of This Invention No. VI'-4 | 648 | 127 | 0.35 | 99 |
| 41 | Compound of This Invention No. VI'-5 | 644 | 126 | 0.34 | 99 |
| 42 | Compound of This Invention No. VI'-9 | 640 | 131 | 0.35 | 100 |
| 43 | Compound of This Invention No. VI'-14 | 620 | 128 | 0.25 | 98 |
| 44 | Compound of This Invention No. VI'-16 | 637 | 131 | 0.31 | 100 |
| 45 | Compound of This Invention No. VI'-21 | 631 | 124 | 0.32 | 98 |
| 46 | Compound of This Invention No. VI'-24 | 629 | 126 | 0.29 | 97 |
| 47 | Compound of This Invention No. VI'-25 | 630 | 128 | 0.30 | 99 |
| 48 | Compound of This Invention No. VI'-32 | 619 | 121 | 0.20 | 98 |
| 49 | Compound of This Invention No. VI'-39 | 612 | 118 | 0.20 | 100 |
| 50 | Compound of This Invention No. VI'-43 | 617 | 112 | 0.20 | 99 |
| 51 | Compound of This Invention No. IV'-44 | 618 | 120 | 0.22 | 100 |
| 52 | Compound of This Invention No. VI'-45 | 630 | 118 | 0.25 | 100 |
| 53 | Compound of This Invention No. VI'-52 | 625 | 126 | 0.24 | 98 |

As is obvious from Table 2, it is found that every sample having the couplers of the invention has excellent spectral absorption characteristics, because their half band widths are extremely narrower and the irregular absorptions are relatively less than those of the sample having the comparative coupler.

It is further found that every sample having the couplers of the invention may be able to provide solid cyan images, because of the high percentage of residual dyes resulted from the heat and moisture resistance tests.

Figure 3:
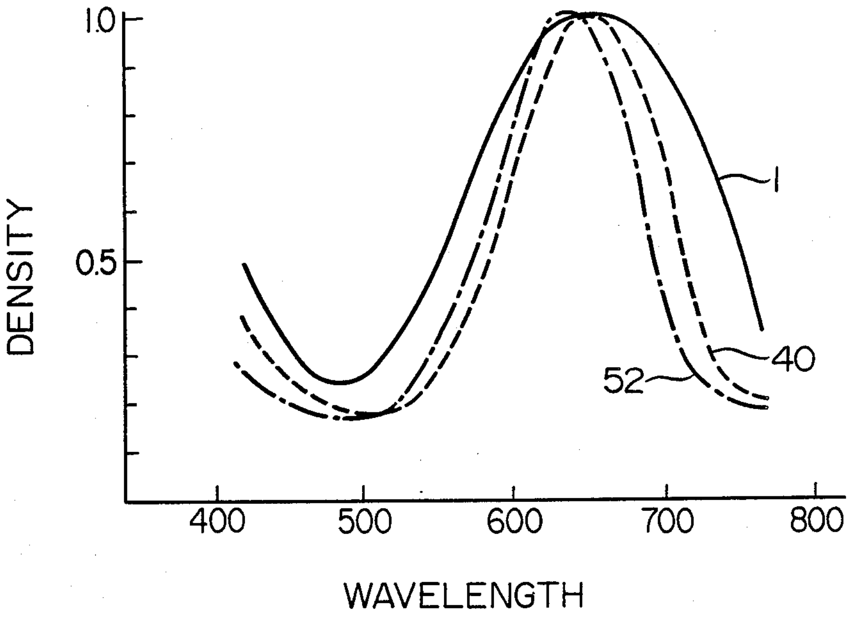
FIG. 3 illustrates the absorption spectra of Samples 1, 40 and 52.

In addition, FIG. 3 shows the fact that the couplers of the invention, i.e., Samples 40 and 52, are relatively less in undesirable irregular absorption caused in green region and relatively sharp in absorption in the regions around λmax, as compared with the conventional phenol type coupler, i.e., Sample 1.

EXAMPLE 3

Samples 54 through 68 of red-sensitive color reversal photographic light-sensitive materials were prepared by coating the following layers over to a triacetyl cellulose film support, in order from the support side.

The amounts of the compounds added are expressed by the amounts thereof per sq. meter unless otherwise specially stated. (Amounts of silver halides are expressed in terms of the contents of silver.)

LAYER 1: AN EMULSION LAYER

A red-sensitive emulsion layer comprising 1.4 g of gelatin, 0.5 g of red-sensitive silver chlorobromide emulsion (containing silver chloride of 96 mol%) and the couplers (in an amount of $9.1\times10^{-4}$ mols) shown in Table 3 dissloved in 0.24 g of dibutyl phthalate.

LAYER 2: A PROTECTIVE LAYER

A protective layer containing 0.5 g of gelatin, whereto 2,4-dichloro-6-hydroxy-s-triazine sodium salt was added as a hardener in an amount of 0.017 g per g of gelatin used.

The resulted Samples were exposed to light through a wedge in an ordinary method and were then processed in the following processing steps.

[Reversal processing steps]

| Step | Time | Temperature |
|---|---|---|
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| | | |
|---|---|---|
| (Primary developer) | | |
| Water | 700 | ml |
| Sodium tetrapolyphosphate | 2 | g |
| Sodium sulfite | 20 | g |
| Hydroquinone. monosulfonate | 30 | g |
| Sodium carbonate, monohydrate | 30 | g |
| 1-phenyl.4 methyl.4-hydroxymethyl-3 pyrazolidone | 2 | g |
| Potassium bromide | 2.5 | g |
| Potassium thiocyanate | 1.2 | g |
| Potassium iodide (in a 0.1% solution) | 2 | ml |
| Water to be added to make | 1000 | ml |
| pH to be adjusted to | pH 10.1 | |
| (Reversal bath) | | |
| Water | 700 | ml |
| Hexasodium nitrilo-N.N.N-trimethylene phosphonate | 3 | g |
| Stannous chloride, dihydrate | 1 | g |
| p-aminophenol | 0.1 | g |
| Sodium hydroxide | 5 | g |
| Glacial acetic acid | 15 | ml |
| Water to be added to make | 1000 | ml |
| (Color developer C) | | |
| Water | 700 | ml |
| Sodium tetrapolyphosphate | 2 | g |
| Sodium sulfite | 7 | g |
| Sodium tertiary phosphate, dodecahydrate | 36 | g |
| Potassium bromide | 1 | g |
| Potassium iodide (in a 0.1% solution) | 90 | ml |
| Sodium hydroxide | 3 | g |
| Citrazinic acid | 1.5 | g |
| N-ethyl-N-(β-methanesulfonamidoethyl)-3-methyl-4-aminoaniline.sulfate | 11 | g |
| Ethylenediamine | 3 | g |
| Water to be added to make | 1000 | ml |
| (Adjuster) | | |
| Water | 700 | ml |
| Sodium sulfite | 12 | g |
| Sodium ethylenediaminetetraacetate, dihydrate | 8 | g |
| Thioglycerol | 0.4 | ml |
| Glacial acetic acid | 3 | ml |
| Water to be added to make | 1000 | ml |
| (Bleaching bath) | | |
| Water | 500 | ml |
| Sodium ethylenediaminetetraacetate, dihydrate | 2.0 | g |
| Ferriammonium ethylenediamine-tetraacetate, dihydrate | 120.0 | g |
| Potassium bromide | 100.0 | g |
| Water to be added to make | 1000 | ml |
| (Fixer) | | |
| Water | 800 | ml |
| Ammonium thiosulfate | 80.0 | g |
| Sodium sulfite | 5.0 | g |
| Sodium hydrogensulfite | 5.0 | g |
| Water to be added to make | 1000 | ml |
| (Stabilizer) | | |
| Water | 800 | ml |
| Formalin (at 37 wt %) | 5.0 | ml |
| Water to be added to make | 1000 | ml |

With each of the processed samples, the maximum spectral absorption wavelength (λmax) and the half band width (W½) were measured in the same manner as in Example 1. The results thereof are shown in Table-3.

In this Example 3, the various measurements including the transmission density measurements were made with a densitometer, Model KD-7R.

TABLE 3

| Sample No. | Coupler used | λmax (nm) | W1/2 | Dλ420 | Residual dye (%) |
|---|---|---|---|---|---|
| 54 | Comparative a | 652 | 168 | 0.46 | 61 |
| 55 | Compound of This Invention No. I'-5 | 630 | 88 | 0.25 | 98 |
| 56 | Compound of This Invention No. I'-19 | 624 | 82 | 0.21 | 100 |
| 57 | Compound of This Invention No. I'-23 | 613 | 80 | 0.21 | 100 |
| 58 | Compound of This Invention No. I'-24 | 619 | 83 | 0.18 | 99 |
| 59 | Compound of This Invention No. I'-31 | 616 | 88 | 0.21 | 98 |
| 60 | Compound of This Invention No. I'-42 | 609 | 79 | 0.19 | 99 |
| 61 | Compound of This Invention No. I'-43 | 608 | 82 | 0.19 | 98 |
| 62 | Compound of This Invention No. I'-63 | 625 | 90 | 0.21 | 100 |
| 63 | Compound of This Invention No. I'-76 | 630 | 91 | 0.22 | 100 |
| 64 | Compound of This Invention No. II'-5 | 629 | 81 | 0.22 | 99 |
| 65 | Compound of This Invention No. II'-9 | 620 | 79 | 0.20 | 100 |
| 66 | Compound of This Invention No. III'-1 | 635 | 74 | 0.20 | 100 |
| 67 | Compound of This Invention No. III'-8 | 617 | 75 | 0.16 | 99 |
| 68 | Compound of This Invention No. IV'-3 | 614 | 107 | 0.35 | 96 |

As is obvious from Table 3, it is found that every sample having the couplers of the invention has excellent spectral absorption characteristics and excellent color reproducibility, because their half band widths are extremely narrower and their irregular absorptions are also less as compared with those of the sample having the comparative coupler.

It is also found that the Samples used the couplers of the invention may be able to provide solid cyan images, because of the extremely high percentage of the residual dye-images resulted from the heat resistance tests.

EXAMPLE 4

Samples 69 through 74 were prepared in the same manner as in Example 3, except that 0.24 g of dibutyl phthalate used in Layer 1 of Example 3 were replaced by 1.65 of dioctyl phenylphosphate.

These samples were exposed and processed in the same manners as in Example 3. The absorption characteristics and the heat and moisture resistance of the images thus obtained were measured.

The results thereof will be shown in Table-4, below.

TABLE 4

| Sample No. | Coupler used | λmax (nm) | W1/2 | Dλ420 | Residual dye (%) |
|---|---|---|---|---|---|
| 69 | Comparative a | 650 | 168 | 0.48 | 62 |
| 70 | Compound of This Invention No. 10 | 643 | 98 | 0.32 | 100 |
| 71 | Compound of This Invention No. 20 | 630 | 94 | 0.27 | 98 |
| 72 | Compound of This Invention No. 26 | 617 | 81 | 0.21 | 100 |
| 73 | Compound of This Invention No. 47 | 629 | 92 | 0.26 | 99 |
| 74 | Compound of This Invention No. 50 | 627 | 83 | 0.21 | 98 |

As is obvious from Table 4, it is found that every sample having the couplers of the invention has excellent spectral absorption characteristics and provides cyan images having an excellent color reproducibility, because the half band widths are extremely narrower, the Dλ420 values are less and the irregular absorptions are also less, as compared with those of the sample having the comparative coupler.

It is also found that the samples used the couplers of the invention may be able to provide solid cyan images, because of the extremely high percentage of the residual dye-images resulted from the heat resistance tests.

What is claimed is:

1. A silver halide color photographic light-sensitive material comprising a support having at least one red light-sensitive silver halide emulsion layer, wherein said red light-sensitive silver halide emulsion layer contains at least one cyan dye-forming coupler selected from the group consisting of those represented by Formulas I, II, III, IV, V and VI;

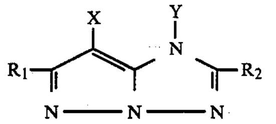
I wherein X represents a hydrogen atom or a substituent capable of being split off upon reaction with the oxidized product of a color developing agent, Y represents a hydrogen atom or a substituent, and $R_1$ and $R_2$ independently represent a hydrogen atom, a substituent or a group having an —NH group provided that at least one of $R_1$ and $R_2$ is a group having an —NH—group;

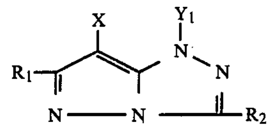
II

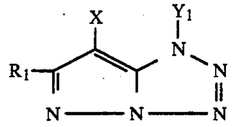
III

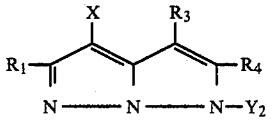
IV

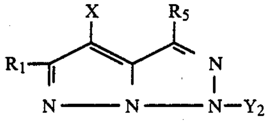
V wherein in Formulas II through V $R_1$ represents a group having an —NH group, $R_2$, $R_3$, $R_4$, $R_5$, $Y_1$ and $Y_2$ independently represent a hydrogen atom or a substituent, and X represents a hydrogen atom or a group capable of being split off upon reaction with the oxidized product of a color developing agent:

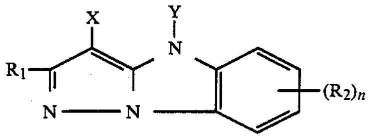
VI wherein $R_1$ represents a group having an —NH group, $R_2$ represents a substituent, n is an integer of from 0 to 4, provided that, when n is 2 or more, respective $R_2$'s may be the same with or different from each other, X represents a hydrogen atom or a substituent capable of being split off upon reaction with the oxidized product of a color developing agent, and Y represents a hydrogen atom or a substituent.

2. The silver halide color photographic light-sensitive material of claim 1, wherein said —NH-group is capable of forming a hydrogen bond with a nitrogen atom in the pyrazoloazole ring, pyrazolotriazole ring or the pyrazolobenzimidazole ring of formulas I through VI.

3. The silver halide color photographic light-sensitive material of claim 1, wherein said group having said —NH—group I is selected from the group consisting of those represented by the formulas:

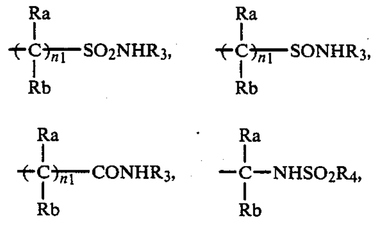

-continued

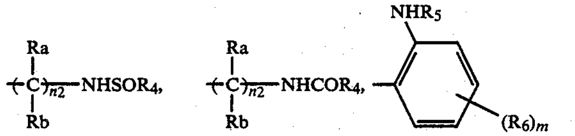

wherein, Ra, Rb, $R_3$, $R_4$, $R_5$ and $R_6$ each represent a hydrogen atom or a substituent, $n_1$ is an integer of zero or 1, $n_2$ is 1 or 2 and m is an integer of 0 to 4, provided that when m is not less than 2, every $R_6$ may be the same as or different from each other.

4. The silver halide color photographic light-sensitive material of claim 3, wherein said Ra and Rb in formula I are independently selected from the group consisting of a hydrogen atom, an alkyl group, an aryl group and a heterocyclic residual group; $R_3$ in formula I is selected from the group consisting of a hydrogen atom, an alkyl group, an aryl group, a heterocyclic residual group, a sulfonyl group, a sulfinyl group, a carbonyl group; $R_4$ is selected from the group consisting of a hydrogen atom, an alkyl group, an aryl group, a heterocyclic residual group; $R_5$ is selected from the group consisting of a hydrogen atom, an alkyl group, an aryl group, a heterocyclic residual group, a sulfonyl group, a sulfinyl group and a carbonyl group; and $R_6$ is a hydrogen atom or a substituent.

5. The silver halide photographic light-sensitive material of claim 4, wherein said $R_1$ and $R_2$ in formula I are selected from the group consisting of an alkyl group, an aryl group, an anilino group, an acylamino group, a sulfonamido group, an alkylthio group, an arylthio group, an alkenyl group, a cycloalkyl group, a halogen atom, a cycloalkenyl group, an alkynyl group, a heterocyclic group, a sulfonyl group, a sulfinyl group, a phosphonyl group, an acyl group, a cyano group, an alkoxy group, an aryloxy group, a heterocyclic-oxy group, a siloxy group, an acyloxy group, a carbamoyloxy group, an amino group, an alkylamino group, an imido group, a ureido group, a sulfamoylamino group, an alkoxy-carbonylamino group, an aryloxycarbonylamino group, an alkoxycarbonyl group, an aryloxycarbonyl group, a heterocyclic-thio group, a spiro compound residual group and a cross-linked hydrocarbon compound residual group.

6. The silver halide color photographic light-sensitive material of claim 4, wherein one of $R_1$ and $R_2$ in formula I is an electron withdrawing group.

7. The silver halide color photographic light-sensitive material of claim 6, wherein said electron withdrawing group is selected from the group consisting of a sulfonyl group, a sulfinyl group, a sulfonyloxy group, a phosphoryl group, a pyrrolyl group, a tetrazolyl group, a cyano group, an acyl group, an acyloxy group, a carboxyl group, an oxycarbonyl group, a nitro group and a halogen atom.

8. The silver halide color photographic light-sensitive material of claim 5, wherein said substituent capable of being split off upon reaction with the oxidized product of a color developing agent in formula I is selected from the group consisting of a halogen atom, an alkoxy group, an aryloxy group, a heterocyclic-oxy group, an acyloxy group, a sulfonyloxy group, an alkoxycarbonyloxy group, an aryloxycarbonyl group, an alkyloxalyloxy group, an alkoxyoxalyloxy group, an alkylthio group, an arylthio group, a heterocyclicthio group, an alkyloxythiocarbonylthio group, an acylamino group, a sulfonamido group, a nitrogen-containing heterocyclic ring bonded to an N atom, an alkyloxycarbonylamino group, an aryloxycarbonylamino group, a carboxyl group, and a group of the formula

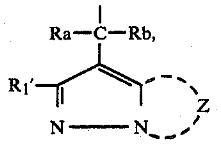

wherein $R_1'$ is synonymous with the aforegiven $R_1$ and/or $R_2$; Ra, and Rb, each represent a hydrogen atom, an aryl group, an alkyl group or a heterocyclic group; and Z represents a group of non-metal atoms necessary to complete a nitrogencontaining heterocyclic ring selected from the group consisting of a pyrazole ring, an imidazole ring, a triazole ring, or tetrazole ring.

9. The silver halide color photographic light-sensitive material of claim 1, wherein said group having said —NH—group in formulas through II through V is selected from the group consisting of those represented by the following formulas;

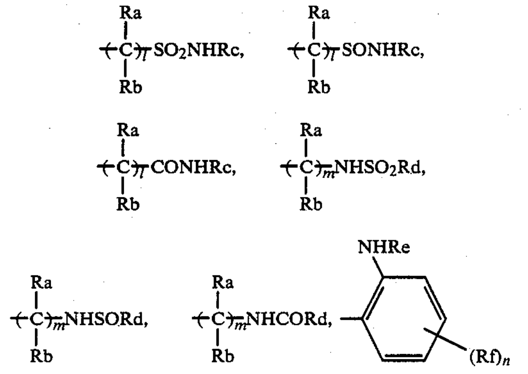

wherein Ra, Rb, Rc, Rd, Re and Rf each represent a hydrogen atom or a substituent, l is an integer of zero or 1 , m is 1 or 2 and n is an integer of 0 through 4, provided that, when n is 2 or more, respective Rf's may be the same as or different from each other.

10. The silver halide color photographic light-sensitive material of claim 9, wherein Ra and Rb in formulas II through IV through are independently selected from the group consisting of a hydrogen atom, an alkyl group, an aryl group, a heterocyclic residual group; Rc is selected from the group consisting of a hydrogen atom, an alkyl group, an aryl group, a heterocyclic residual group, a sulfonyl group, a sulfinyl group and a carbonyl group; and Rd is selected from the group consisting of a hydrogen atom, an alkyl group, an aryl group and a heterocyclic residual group; Re is selected from the group consisting of a hydrogen atom, an alkyl group, an aryl group, a heterocyclic residual group, a sulfonyl group, a sulfinyl group, a carbonyl group; and Rf represents a hydrogen atom and a substituent.

11. The silver halide color photographic light-sensitive material of claim 10, wherein $R_2$, $R_3$, $R_4$ and $R_5$ in formulas through II through IV are selected from the group consisting of an alkyl group, an aryl group, an anilino group, an acylamino group, a sulfonamido group, an alkylthio group, an arylthio group, an alkenyl group, a cycloalkyl group, a halogen atom, a cycloalkenyl group, an alkynyl group, a heterocyclic group, a sulfonyl group, a sulfinyl group, a phosphonyl group, an acyl group, a carbamoylsulfamoyl group, a cyano group, an alkoxy group, an aryloxy group, a hetercyclic-oxy group, a siloxy group, an acyloxy group, a carbamoyloxy group, an amino group, an alkylamino group, an imido group, a ureido group, a sulfamoylamino group, an alkoxycarbonylamino group, an aryloxcarbonylamino group, an alkoxycarbonyl group, an aryloxycarbonyl group, heterocyclic-thio group, a spiro compound residual group and a cross-linked hydrocarbon compound residual group.

12. The silver halide color photographic light-sensitive material fo claim 9, wherein $R_2$, $R_3$, $R_4$ and $R_5$ in formulas through II through IV is an electron withdrawing group.

13. The silver halide color photographic light-sensitive material of claim 12, wherein said electron withdrawing group is selected from the group consisting of a sulfonyl group, a sulfinyl group, a sulfonyloxy group, a phosphoryl group, a pyrrolyl group, a tetrazolyl group, a cyano group, an acyl group, an acyloxy group, a carboxyl group, an oxycarbonyl group, a nitro group and a halogen atom.

14. The silver halide color photographic light-sensitive material of claim 9, wherein said substituent capable of being split off upon reaction with the oxidized product of a color developing agent in formulas through II through IV is selected from the group consisiting of a halogen atom, an alkoxy group, an aryloxy group, a heterocyclic-oxy group, an acyloxy group, a sulfonyloxy group, an alkoxycarbonyloxy group, an aryloxycarbonyl group, an alkyloxalyloxy group, an alkoxyoxalyloxy group, an alkylthio group, an arylthio group, a heterocyclic-thio group, an alkyloxythiocarbonylthio group, an acylamino group, a sulfonamido group, a nitrogen-containing heterocyclic ring bonded to an N atom, an alkyloxycarbonylamino group, an aryloxycarbonylamino group, a carboxyl group, and a group of the formula:

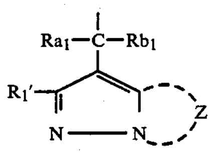

wherein $R_1'$ is synonymous with the aforegiven $R_1$ and/or $R_2$; $Ra_1$ and $Rb_1$ each represent a hydrogen atom, an aryl group, an alkyl group or a heterocyclic group; and Z represents a group of non-metal atoms necessary to complete a nitrogen-containing heterocyclic ring selected from the group consisting of a pyrazole ring, an imidazole ring, a triazole ring, and a tetrazole ring.

15. The silver halide color photographic light-sensitive material of claim 1, wherein said group having an —NH—group in formula VI is selected from the group consisting of those represented by the following formulas;

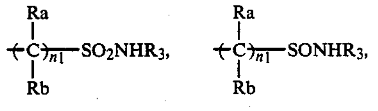

-continued

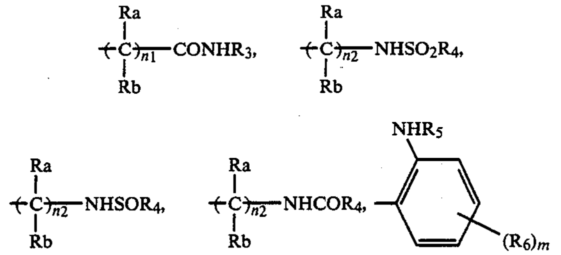

wherein Ra, Rb, $R_3$, $R_4$ and $R_5$ independently represent a hydrogen atom or a substituent, $R_6$ represents a substituent, $n_1$ is an integer of zero or 1, $n_2$ is 1 or 2 and m is an integer of 0 through 4 provided that when m is 2 or more, respective $R_6$'s may be the same as or different from each other.

16. The silver halide color photographic light-sensitive material of claim 15, wherein Ra, Rb and $R_4$ in formula VI are independently selected from the group consisting of a hydrogen atom, an alkyl group, an aryl group, a heterocyclic residual group; $R_3$ in formula VI is selected from the group consisting of a hydrogen atom, an alkyl group, an aryl group, a heterocyclic residual group and, a sulfonyl group, a sulfinyl group and a carbonyl group; and $R_5$ in formula is selected from the group consisting of a hydrogen atom, an alkyl group, an aryl group, a heterocyclic residual group, a sulfonyl group, a sulfinyl group, and a carbonyl group.

17. The silver halide color photographic light-sensitive material of claim 16, wherein $R_2$ in formula VI is selected from the group consisting of an alkyl group, an aryl group, an anilino group, an acylamino group, a sulfonamido group, an alkylthio group, an arylthio group, an alkenyl group, a cylcoalkyl group, a halogen atom, a cycloalkenyl group, an alkynyl group, a heterocyclic group, a sulfonyl group, a sulfinyl group, a phosphonyl group, an acyl group, a carbamoylsulfamoyl group, a cyano group, an alkoxy group, an aryloxy group, a hetercyclic-oxy group, a siloxy group, an acyloxy group, a carbamoyloxy group, an amino group, an alkyl-amino group, an imido group, a ureido group, a sulfamoylamino group, an alkoxycarbonylamino group, an aryloxycarbonylamino group, an alkoxycarbonyl group, an aryloxycarbonyl group, heterocyclic-thio group, a spiro compound residual group and a cross-linked hydrocarbon compound residual group.

18. The silver halide color photographic light-sensitive material of claim 15, wherein $R_2$ in formula is an electron withdrawing group.

19. The silver halide color photographic light-sensitive material of claim 18, wherein said electron withdrawing group is selected from the group consisting of a sulfonyl group, a sulfinyl group, a sulfonyloxy group, a phosphoryl group, a pyrrolyl group, a tetrazolyl group, a cyano group, an acyl group, an acyloxy group, a carboxyl group, an oxycarbonyl group, a nitro group and a halogen atom.

20. The silver halide color photographic light-sensitive material of claim 15, wherein said substituent capable of being split off upon reaction with the oxidized product of a color developing agent in formula is selected from the group consisting of a halogen atom, an alkoxy group, an aryloxy group, a heterocyclic-oxy group, an acyloxy group, a sulfonyloxy group, an alkoxylcarbonyl group, an aryloxy carbonyl group, an alkyloxalyoxy group, an alkoxyoxalyloxy group, an alkylthio group, an arylthio group, a heterocyclic-thio group, an alkyloxythiocarbonylthio group, an acylamino group, a sulfonamido group, a nitrogen-containing heterocyclic ring bonded to an N atom, an alkyloxycarbonylamino group, an aryloxycarbonylamino group, a carboxyl group, and a group of the formula.

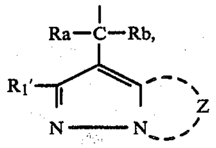

wherein $R_1'$ is synonymous with the aforegiven $R_1$ and/or $R_2$; Ra, and Rb, each represent a hydrogen atom, an aryl group, an alkyl group or a heterocyclic group; and Z represents a group of non-metal atoms necessary to complete a nitrogen-containing heterocyclic ring selected from the group consisting of a pyrazole ring, an imidazole ring, a triazole ring, and a tetrazole ring.

* * * * *